United States Patent [19]

Sakashita et al.

[11] Patent Number: 5,088,998
[45] Date of Patent: Feb. 18, 1992

[54] RESECTOSCOPE APPARATUS

[75] Inventors: Kiyotoshi Sakashita, Hachioji; Shinichi Nishigaki, Tokyo; Shiro Bito, Hachioji, all of Japan

[73] Assignee: Olympus Optical Co., Ltd., Tokyo, Japan

[21] Appl. No.: 355,725

[22] Filed: May 23, 1989

[30] Foreign Application Priority Data

Sep. 16, 1988 [JP] Japan ................. 63-231871
Feb. 28, 1989 [JP] Japan ................... 1-49041

[51] Int. Cl.$^5$ ............................. A61B 17/36
[52] U.S. Cl. ............................. 606/46; 128/6
[58] Field of Search ............ 606/39, 40, 45–47; 128/4, 6, 7

[56] References Cited

U.S. PATENT DOCUMENTS

| | | | |
|---|---|---|---|
| 3,939,839 | 2/1976 | Curtiss | 606/46 |
| 3,939,840 | 2/1976 | Storz . | |
| 3,990,456 | 11/1976 | Iglesias | 606/46 |
| 4,149,538 | 4/1979 | Mrava et al. | 606/46 |
| 4,524,770 | 6/1985 | Orandi | 606/46 |
| 4,538,610 | 9/1985 | Kubota | 606/46 |
| 4,648,399 | 3/1987 | Nakada | 606/46 |
| 4,657,018 | 4/1984 | Hakky | 606/46 |
| 4,726,370 | 2/1988 | Karasawa et al. . | |
| 4,744,361 | 5/1988 | Karasawa | 128/4 X |

FOREIGN PATENT DOCUMENTS

| | | |
|---|---|---|
| 7327364 | 1/1974 | Fed. Rep. of Germany . |
| 7118059 | 6/1975 | Fed. Rep. of Germany . |
| 3735945A1 | 5/1988 | Fed. Rep. of Germany . |
| 62-155843 | 7/1987 | Japan . |

Primary Examiner—Robert A. Hafer
Assistant Examiner—Kerry Owens
Attorney, Agent, or Firm—Armstrong, Nikaido, Marmelstein, Kubovcik & Murray

[57] ABSTRACT

The resectoscope apparatus of this invention is provided with an electrode resecting or coagulating tissues within a body cavity by using a high frequency curent, a sheath in which at least a part of a hollow tube part inserting the electrode is formed of an electric insulating material, an operating part making the electrode operatable from outside the body, enclosing the electrode together with the sheath and formed of an electric insulating material and an endoscope inserted through the sheath to be able to observe the body cavity interior.

18 Claims, 28 Drawing Sheets

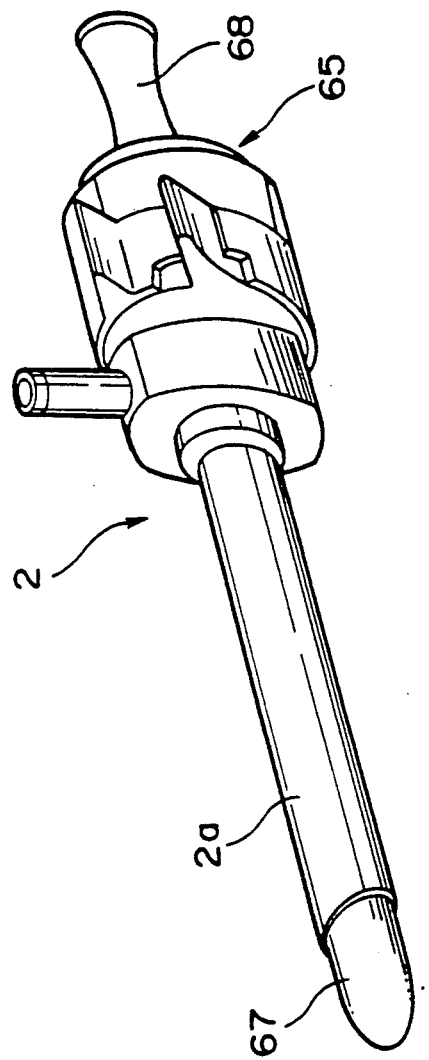

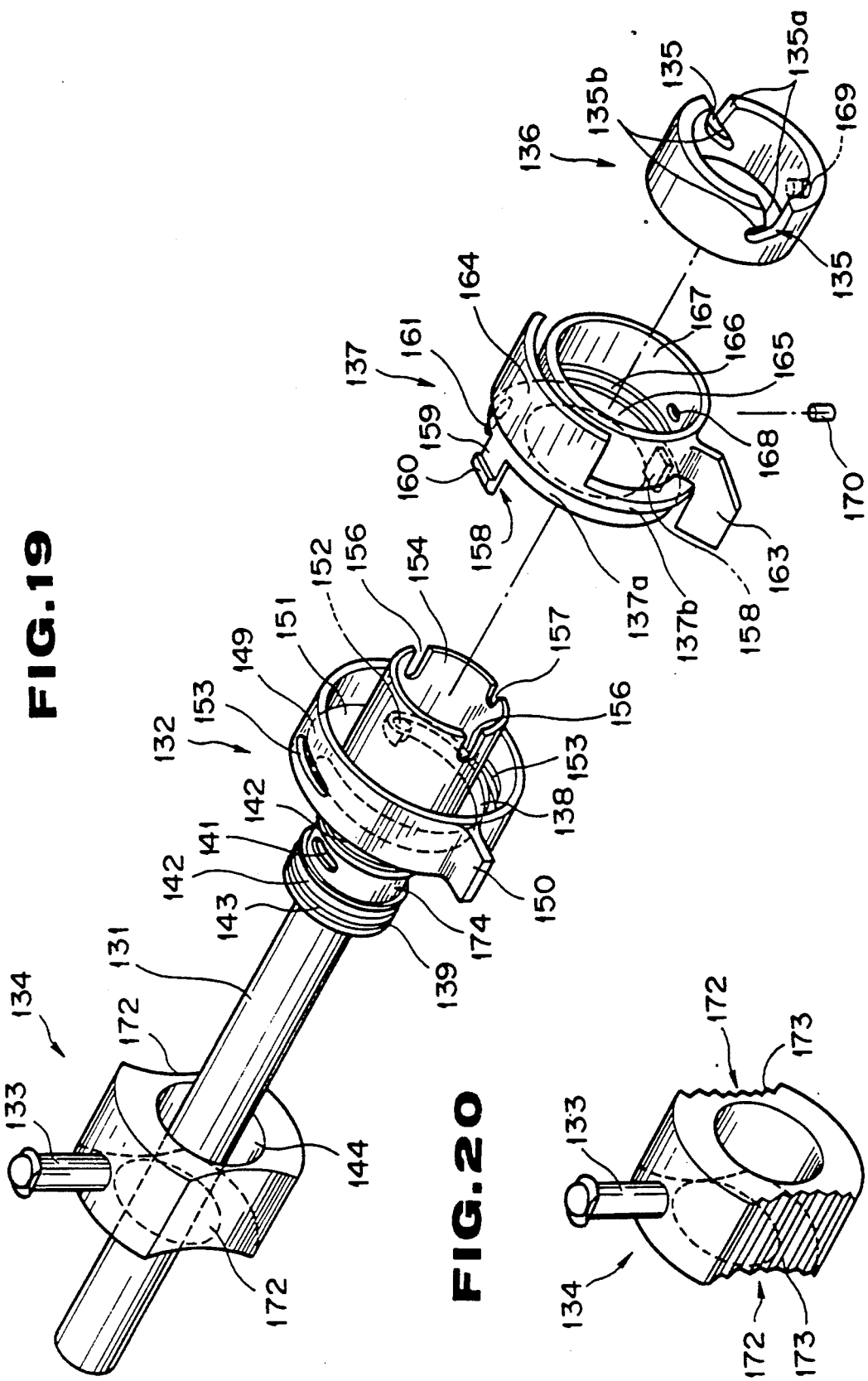

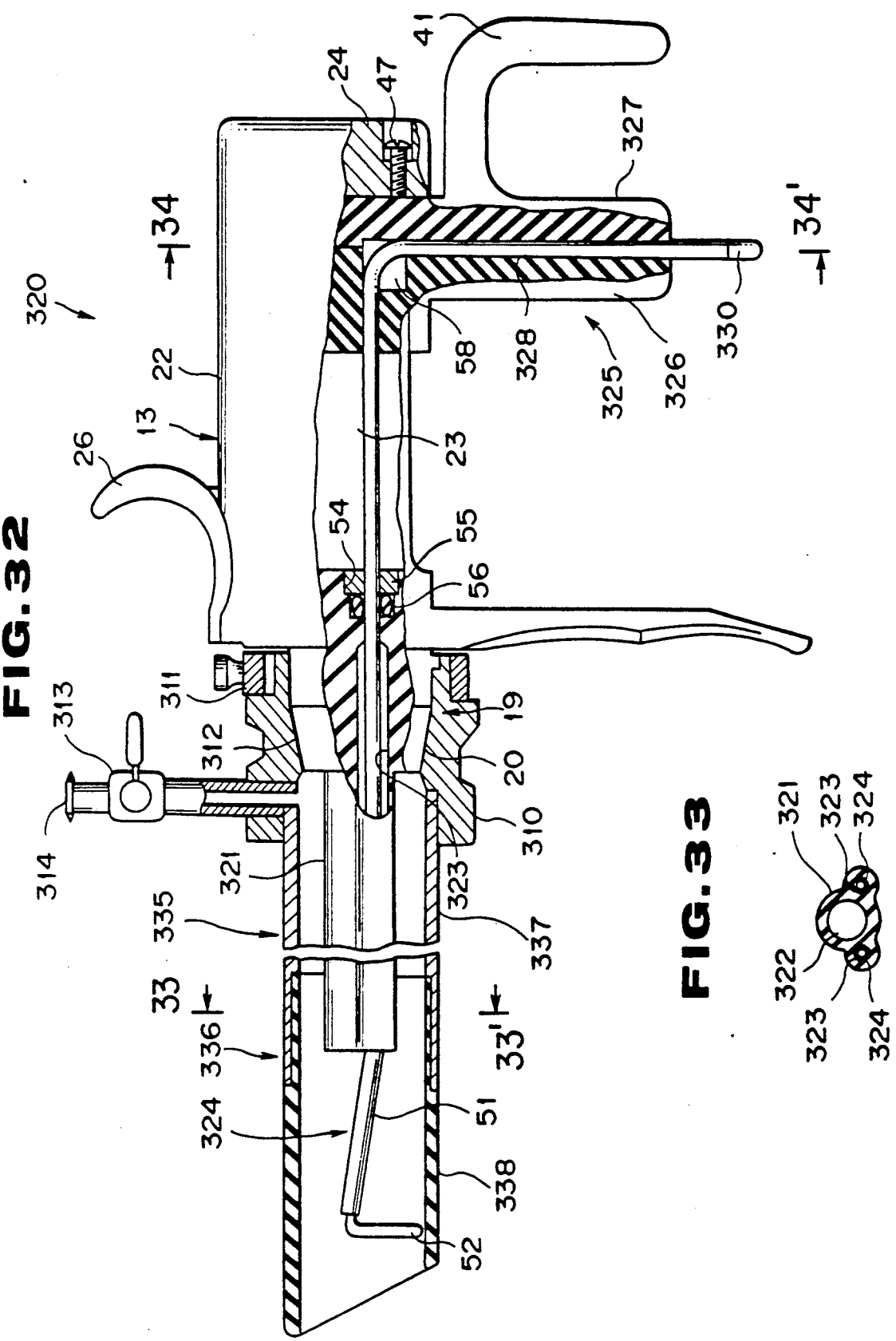

RESECTOSCOPE APPARATUS

FIELD AND BACKGROUND OF THE INVENTION

This invention relates to a resectoscope apparatus for resecting and coagulating tissues within a body cavity.

Recently, there is extensively utilized an endoscope apparatus whereby internal organs within a body cavity can be observed by inserting an elongate insertable part into the body cavity or various therapeutic treatments can be made, as required, by using treating instruments inserted through a treating instrument channel.

As the above mentioned endoscope apparatus, there is a high frequency endoscope apparatus for resecting a prostate, uterus interior, ureter interior or renal pelvis interior. As such a high frequency endoscope apparatus, there is a resectoscope apparatus whereby treatment for the resection of a prostate can be made by inserting the insertable part into the bladder through the urethra and passing a high frequency electric current through a resecting electrode as shown, for example, in the publication of a Japanese Utility Model Application No. 149616/1985.

Generally, a resectoscope apparatus comprises a hollow sheath to be inserted into a body cavity, an operating part having a slider removably fitted to the rear end side of this sheath and an observing scope (optical sighting tube) removably fitted from the rear end side of this operating part. An electrode can project out of and retract into the rear end side of this operating part. The electrode is made like a loop and is branched into two branches at the tip for the resection of tissues within a body cavity. The operating part is provided with a guide tube made of a metal in order to insert the scope. The guide tube projects forward from the sheath connecting part of the operating part, and is inserted into the sheath and provided on the outer periphery rearward from the sheath connecting part with the above mentioned slider so as to be slidable forward and rearward. An electrode inserting tube, inserting and guiding the above mentioned electrode, is provided in parallel with the guide tube. The electrode inserted through this electrode inserting tube is inserted further into an electrode inserting hole of the above mentioned slider and is fixed to an electric contact within the slider. When the electrode is in contact with an affected part and the slider is moved forward and rearward while a high frequency electric current flows, with the forward and rearward movements of the electrode, the affected part will be able to be resected or coagulated.

Since the sheath is inserted into the body cavity, in order to reduce the invasion on the body cavity side, the outside diameter of the sheath must be made as small as possible.

On the other hand, since the optical sighting tube for observing the affected part must also be inserted into the sheath inserting part, in order to observe performance, the larger the optical sighting tube diameter, the better. Since an irrigating liquid is fed into the body cavity through the sheath inserting part as a tube path, in order to secure a clean visual field, sufficient liquid must be input and a space as large as possible must be prepared for the irrigating liquid.

Under such circumstances, the outside diameter of the electrode inserted into the sheath is also restricted. The insulating coating of the electrode can not be made thick enough and, in case a high frequency current is activated, the insulating coating will often be destroyed.

If the insulating coating of the electrode is destroyed, in the conventional resectoscope apparatus, electric current will leak to the patient and the operator from the conductive material coming out to the shielding part of the resectoscope apparatus through the conductive material such as a metal near the destroyed insulating part.

Even if the insulation is not destroyed, since a high frequency current (usually of several 100 $KH_z$) is used, even if the coating member of the electrode inserted through the sheath is sufficiently insulated from direct current, when the disinfection with chemicals is repeated, the insulation from high frequencies will be greatly reduced. Thus, when the insulation of the sheath from the electrode through which the high frequency current flows, is reduced, the high frequency current will flow to the inside wall of the body cavity of the patient into which the sheath is inserted and no sufficient safety will be secured.

Also, in case the resecting electrode is inserted through the sheath, if the electrode is bent, it may contact the inside wall surface of the sheath. In such a case, even if the insulation from the direct current is kept by the coating material, the high frequency current may leak out to the sheath side through a minute capacity.

For the purpose of preventing the electric current from leaking out to the patient and operator, there are suggested by the present applicant, for example, a Japanese Patent Application No. 23186/1988 wherein the guide tube of the operating part is formed of an insulating material or the connecting part of the operating part is formed of an insulating material and a Japanese Patent Application No. 292919/1985 wherein at least the inside diameter or outside diameter of the inserted part of the sheath jacket tube is provided with a ceramic layer.

However, in the above mentioned art, somewhere in the sheath and operating part of the resectoscope, conductive material such as a metal has been used in a component part which is likely to contact the patient and operator.

Therefore, leaking current by the minute high frequency capacity, by the reduction of the high frequency insulation of the insulating coating part of the electrode or by the insulation destruction of the insulating coating part of the electrode as is described above can never be made to reach the patient and operator. A further problem is that, even if the respective parts are separately partly made of an insulating material, if conductive material as a metal is used in a part, the leaking current will concentrate on this conductive material by avoiding the other insulating materials and, if the patient or operator touches the conductive material, the current density will become larger, a burn or shock will likely be generated and it will be rather dangerous.

OBJECT AND SUMMARY OF THE INVENTION

An object of the present invention is to provide a resectoscope apparatus whereby, in a surgical operation, when the patient or operator touches a conductive material such as a metal of a sheath jacket tube or operating part, the leaking current will be stopped, and there will be no danger such as a burn or electric shock so that safety will be high.

The resectoscope apparatus of the present invention comprises an electrode resecting or coagulating tissues within a body cavity by using a high frequency current, a sheath in which a hollow tube part inserting at least an electrode is formed of an electric insulating material and an operating part capable of operating the electrode from outside the body and formed of an electric insulating material enclosing the electrode together with the sheath.

BRIEF DESCRIPTION OF THE DRAWINGS

FIGS. 1 to 16 relate to the first embodiment of the present invention.

FIG. 1 is an appearance view of the whole of a resectoscope apparatus.

FIG. 2 is an appearance view of an operating part having a guide tube formed of an electric insulating material.

FIG. 3 is a sectioned view of an operating part.

FIG. 4 is a sectioned view in the direction 4—4 in FIG. 3.

FIG. 5 is a sectioned view in the direction 5—5 in FIG. 3.

FIG. 6 is an explanatory view of an electrode provided in the operating part.

FIG. 7 is a sectioned view in the direction 7—7 in FIG. 6.

FIG. 8 is an explanatory view of an electrode.

FIG. 9 is an elevation of an electrode provided within a sheath.

FIG. 10 is an appearance view of a sheath combined with a mandolin.

FIG. 11 is a sectioned view of a sheath combined with a mandolin.

FIG. 12 is a sectioned view in the direction 12—12 in FIG. 11.

FIG. 13 is a sectioned view in the direction 13—13 in FIG. 11.

FIG. 14 is a sectioned view in the direction 14—14 in FIG. 12.

FIG. 15 is a disassembled view of respective parts of a sheath.

FIG. 16 is an explanatory view of a cam groove part of a sheath.

FIGS. 17 to 20 relate to the second embodiment of the present invention.

FIG. 17 is a sectioned view of a sheath.

FIG. 18 is a sectioned view in the direction 18—18 in FIG. 17.

FIG. 19 is a disassembled view of a sheath.

FIG. 20 is a view showing a rotary cock knurled on both right and left side surfaces.

FIG. 21 is a perspective view of the whole of an operating part formed of plastic.

FIG. 22 is a sectioned view of a resectoscope apparatus with an electrode and sheath combined in an operating part.

FIG. 23 is a sectioned view in the direction 23—23 in FIG. 22.

FIG. 24 is a sectioned view in the direction 24—24 in FIG. 22.

FIG. 25 is a sectioned view in the direction 25—25 in FIG. 24.

FIG. 26 is a disassembled view, of main members in the rear part of the operating part.

FIG. 27 is a sectioned view in the direction 27—27 in FIG. 22.

FIG. 28 is a perspective view of an optical sighting tube.

FIG. 29 shows a modification of a sheath.

FIGS. 30 to 35 relate to the fourth embodiment of the present invention.

FIG. 30 is an explanatory view of the whole of an operating part in which a guide tube and body are integrally FIG. 31 is a sectioned view of an operating part.

FIG. 32 is an explanatory view of an electrode within an operating part combined with a sheath.

FIG. 33 is a sectioned view in the direction 33—33 in FIG. 32.

FIG. 34 is a sectioned view in the direction 34—34 in FIG. 32.

FIG. 35 is an explanatory view of an electrode.

FIG. 37 is a sectioned view of an operating part.

FIG. 38 is a disassembled view of an operating part.

FIG. 39 is a sectioned view of an operating part.

FIG. 40 is a sectioned view on line 40—40 in FIG. 39.

FIG. 41 is an appearance view of the whole of an operating part.

FIG. 42 is a sectioned side view of the operating part.

FIG. 43 is a sectioned view on line 43—43 in FIG. 42 and shows the structure of a slider part.

FIG. 44 is a sectioned view on line 44—44 in FIG. 42 and shows the structure of an optical sighting tube connecting part.

FIG. 45 is a partly sectioned appearance view as only an electrode part is taken out.

DETAILED DESCRIPTION OF THE PREFERRED EMBODIMENTS OF THE INVENTION

Figure 1:
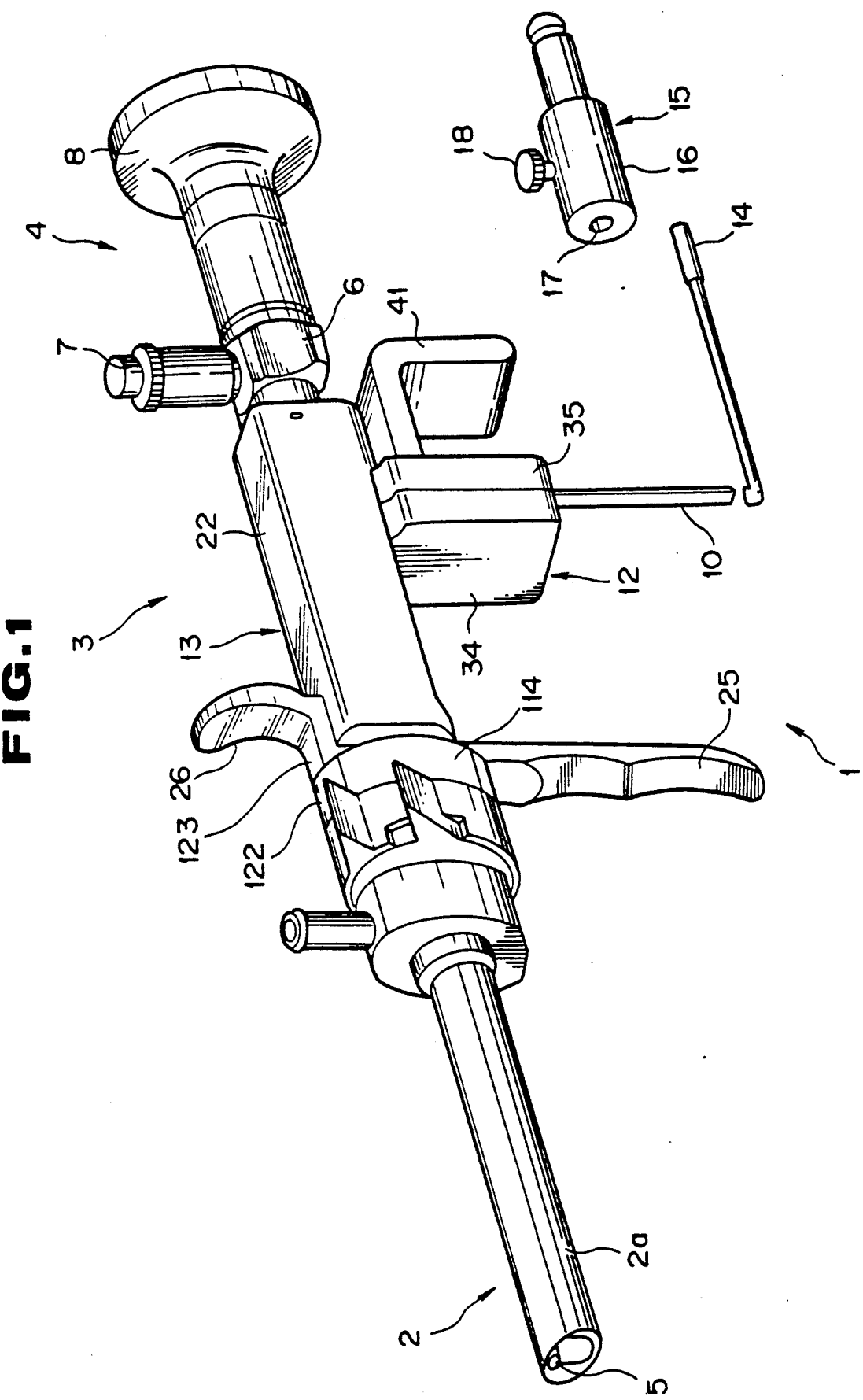

FIGS. 1 to 6 show the first embodiment of the present invention.

A resectoscope apparatus 1 of this embodiment comprises a sheath 2, an operating part 3 removably fitted to the rear of this sheath 2, an observing optical sighting tube 4 inserted through the sheath 2 from the rear of this operating part 3 and an electrode 5 inserted through the sheath 2 from the above mentioned operating part 3.

The above mentioned optical sighting tube 4 consists of an insertable part (not illustrated) inserted into a hollow tube part 2a of the sheath 2 from the operating part 3 and a hand base part 6. A light guide and observing optical system are inserted within this insertable part. A light guide connecting part 7 feeding an illuminating light to the light guide is provided on the side of the hand base part 6. Further, an eyepiece 8 for observing an object image illuminated by an illuminating light transmitted by a light guide (not illustrated) and transmitted by an observing optical system (not illustrated) is provided at the rear end of the hand base part 6.

Figure 2:
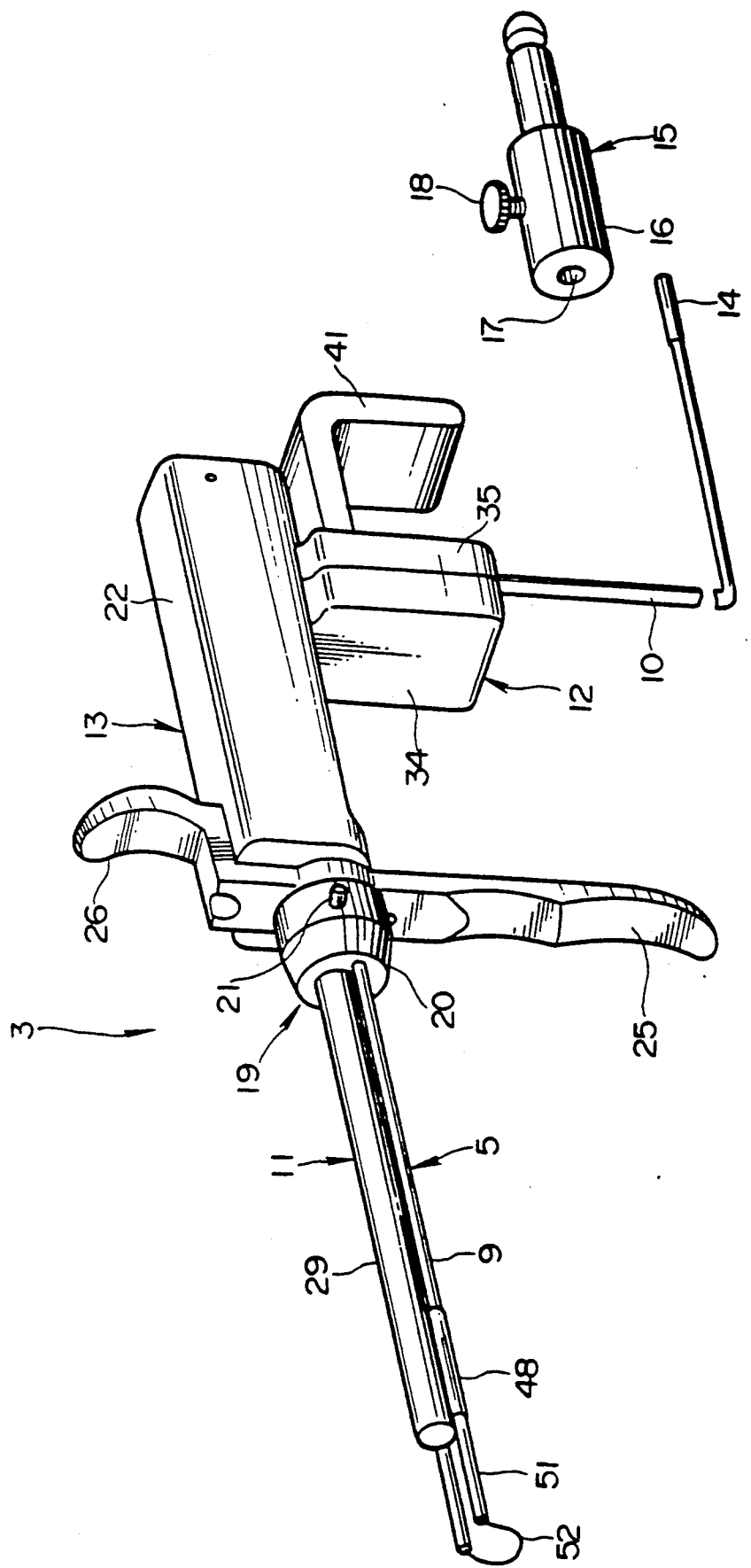

As shown in FIG. 2, in this embodiment, an electrode part 9, cord part 10 and operating part 3 are integrally formed.

The operating part 3 comprises the electrode 5 in which an electrode part 9 and cord part 10 are integrally formed, an optical sighting tube inserting part 11 in which the optical sighting tube 4 is inserted, a slider part 12 sliding the above mentioned electrode 5 in the forward and rearward direction and an operating part body 13.

Further, a rigid part 14 provided at the rear end of the above mentioned cord part 10 is to be removably fixed to a plug 15 electrically and mechanically connected with a high frequency current source (not illustrated). A connecting hole 17 in which the above mentioned rigid part 14 is to be inserted is formed on the end surface of a holding part 16 which is formed to be a columnar electric insulating material of the plug 15. A screw 18, fixing the inserted rigid part 14, is screwed into the peripheral wall surface of plug 15.

In FIG. 3, a sheath connecting part 19 is formed in front of the operating part body 13 forming the operating part 3 and a tapered part 20 smaller in a forward diameter is provided in the front part of this sheath connecting part 19. A pin 21 (FIG. 2) is provided to project in the diametral direction in the rear of the tapered part 20 so that the operating part 3 may be removably watertightly connected with the sheath 2 by the pin 21 and the above mentioned tapered part 20.

A cover 22 of a substantially square cross-sectioned shape is extended in the rear of the sheath connecting part 19 and is provided in the lower part with a groove part 23 in the lengthwise direction. An optical sighting tube connecting part 24 (FIG. 5) is provided in the rear of this groove part 23. A lower finger hanger 25 is provided to project downward between the sheath connecting part 19 and groove part 23 so that, in case the operating part 3 is held with one hand, the middle finger and third finger may be placed and an upper finger hanger 26 on which the forefinger may be placed is provided to project upward in the upper part of the cover 22. Within the above mentioned groove part 23, a spring shaft 27 is extended rearward from the sheath connecting part 19 side and is externally fitted with a wound coil spring 28. The sheath connecting part 19, tapered part 20, pin 21, cover 22, lower finger hanger 25, upper finger hanger 26 and spring shaft 27 are formed of plastic which is an electric insulating material and the parts are integrally molded as molded parts. There can be enumerated electric insulating materials as, for example, polycarbonate (abbreviated as PC), polyacetal (polyoxymethylene) (abbreviated as POM), polyphenylene oxide (abbreviated as PPO), polysulfone (abbreviated as PSU), polyphenylene sulfide (abbreviated as PPS) and polyether imide (abbreviated as PEI).

Below the spring shaft 27 within the groove part 23, a guide tube 29 formed of electric insulating material such as plastic and passing through the above mentioned sheath connecting part 19 is provided in parallel with the spring shaft 27 and is internally fitted in the rear end part into an optical sighting tube inserting hole 30 provided in the above mentioned optical sighting tube connecting part 24 so that the tube path of the guide tube 29 and the optical sighting tube inserting hole 30 ma communicate with each other. An 0-ring 31 is fixed by an 0-ring presser 32 on the inner periphery of the optical sighting tube inserting hole 30 so that the optical sighting tube 4 may be inserted through the guide tube 29 and kept watertight from the to the tip part of the operating part 3.

A slider part 12 is provided within the above mentioned groove part 23 and consists of a slider front part 34 and slider rear part 35 formed of plastic which is an electric insulating material to be of the same upper shape as the internal shape of the groove part 23 so as to be slidable within the groove part 23. A spring hole 36 passes through the slider front part 34 and a shaft hole 37 passes through the slider rear part 35 to communicate with the spring hole 36. Below the spring hole 36 and shaft hole 37, a guide tube hole 38 is provided through the slider front part 34 and slider rear part 35. The above mentioned spring shaft 27 is inserted through the above mentioned shaft hole 37 and spring hole 36 and the above mentioned coil spring 28 is inserted through the spring hole 36 provided in the slider front part 34 and is energized to press the front end surface of the slider rear part 35. The guide tube 29 inserted through the guide tube hole 38 slidably supports the slider part 12.

Holes 39 are provided on the rear end surface of the above mentioned slider front part 34. Snap fits 40 are provided to project in the positions corresponding to the holes 39 on the front end surface of the slider rear part 35 opposed to the rear end surface. The slider front part 34 and slider rear part 35 are made integral by engaging the snap fits 40 respectively with the holes 39.

A thumb hanger 41, on which the thumb can be placed in holding the operating part 3 with one hand, is extended from the rear end surface of the slider rear part 35. When the thumb hanger 41 is pushed forward with the thumb, it will be able to slide the slider part 12 forward against the energizing force of the above mentioned coil spring and, when the force of the thumb is released, the slider part 12 will contact the front end surface of the optical sighting tube connecting part 24 due to the energizing force of the coil spring 28.

A pin hole 43 into which a connecting pin 42 of the optical sighting tube 4 is inserted is provided above the optical sighting tube inserting hole 30 on the rear end surface of the above mentioned optical sighting tube connecting part 24 and passes through a space 44 provided within the optical sighting tube connecting part 24. A piano wire 45 is set substantially at right angles with the lengthwise direction in front of the pin hole 43 within this space 44 so that, when the connecting pin 42 is inserted into the pin hole 43, the piano wire 45 will engage with a groove 46 provided in the connecting pin 42 to removably connect the optical sighting tube 4 to the operating part 3.

Figure 6:
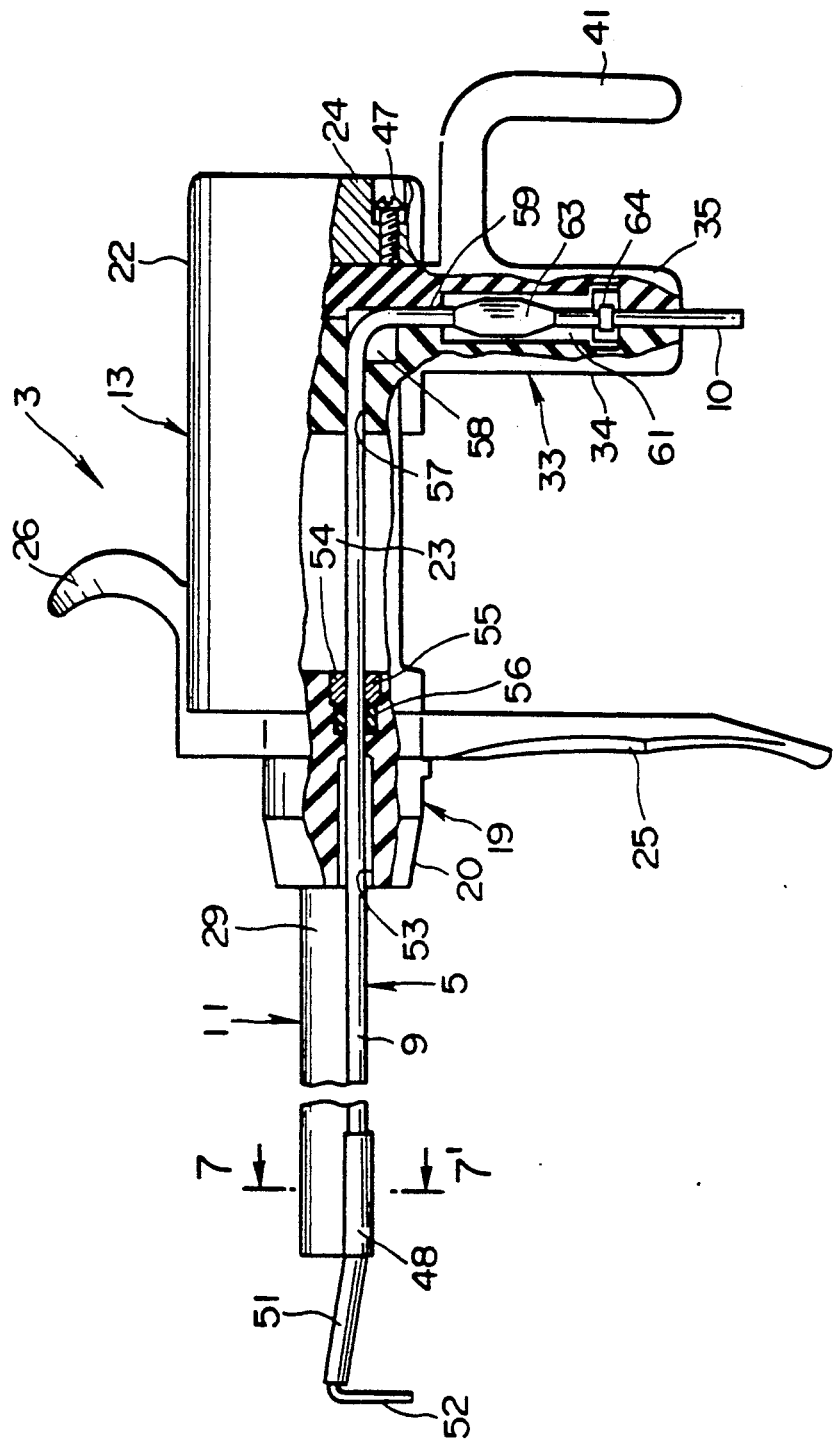
Figure 9:
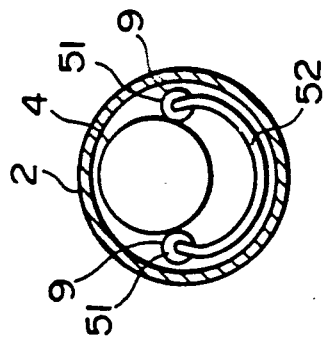

As shown in FIG. 6, a screw 47 is screwed in from the rear end surface of the optical sighting tube connecting part 24 so that the displacement may be adjusted within the groove part 23 of the slider part 12 and is projected at the tip within the groove part 23 so as to contact the rear end surface of the slider part 12.

Figure 8:
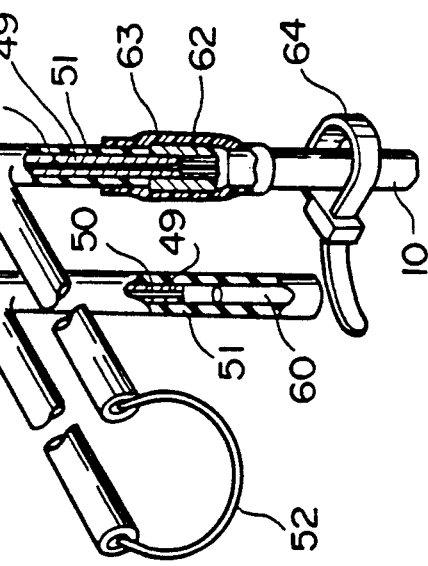
Figure 7:
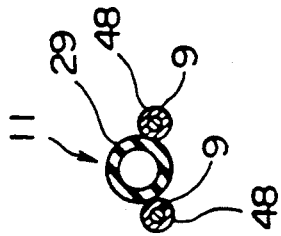
Figure 11:
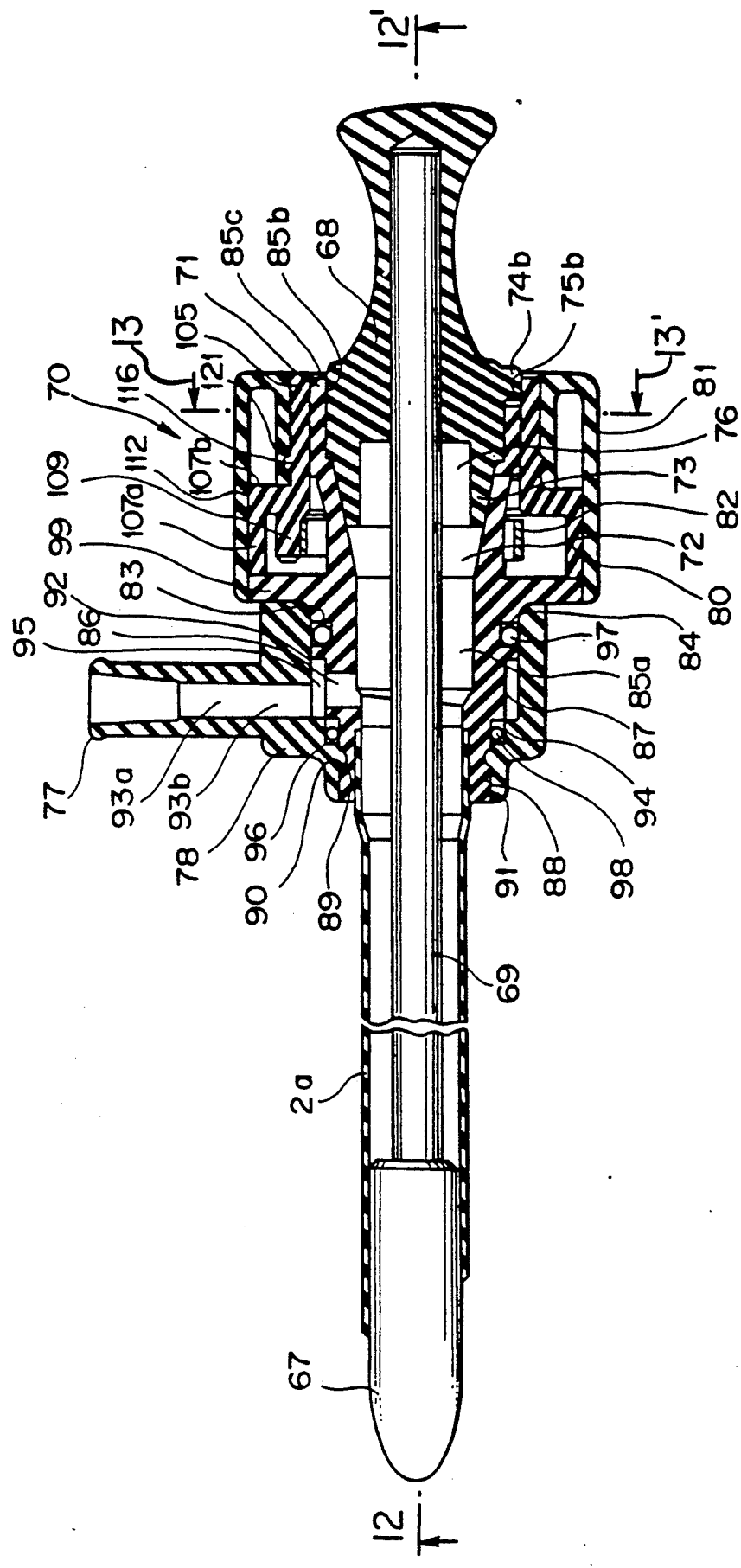
Figure 12:
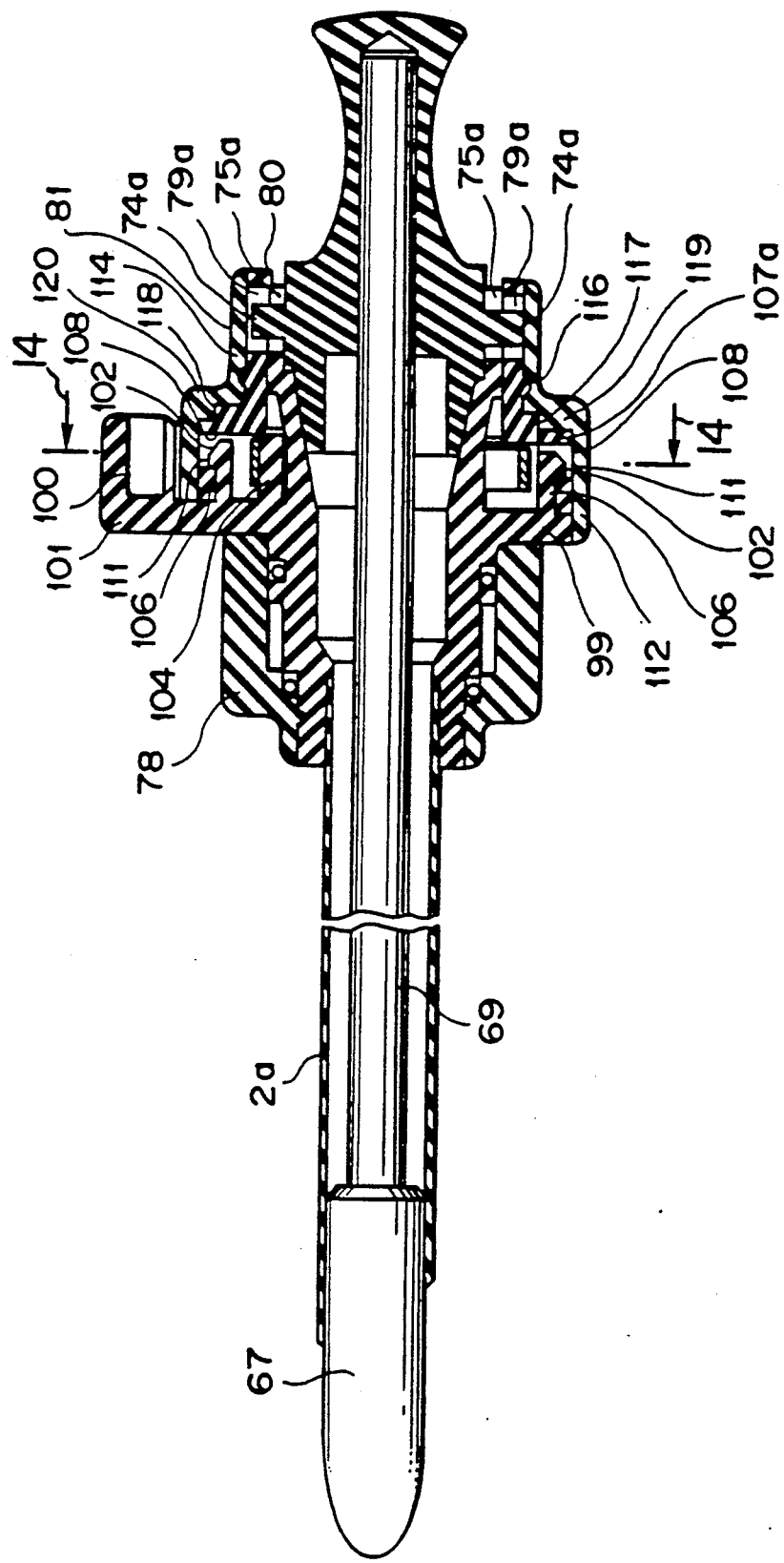

In FIGS. 6 and 7, the electrode parts 9 of the above mentioned electrode 5 are held as inserted respectively through guide pipes 48 provided on both sides of the lower part of the above mentioned guide tube 29, are slidably passed through the sheath connecting part 19 and are then bent downward within the slider part 12. In each electrode part 9, as shown in FIG. 8, a wire 50 passing an electric current is inserted through a stainless steel pipe 49 which is coated on the periphery with a Teflon tube 51 for electric insulation. The front end parts of the respective electrode parts 9 project on the right and left forward of the front end of the guide tube 29 and the wire 50 is exposed from the electric insulating parts. This exposed wire 50 forms a loop 52 of an outside diameter somewhat smaller than the inside diameter of the hollow tube part 2a of the sheath 2 so as to resect tissues within a body cavity when a high frequency current is passed therethrough.

The electrode parts 9 are inserted respectively through inserting holes 53 provided in the sheath connecting part 19 and through O-ring holes 54 communicating respectively with the inserting holes 53. Each O-ring hole 54 is provided with an O-ring 56 fixed with an O-ring presser 55 so that the electrode part 9 may be kept watertight in sliding in the forward and rearward direction. Each electrode 9 is further inserted through an electrode hole 57 provided in the slider front part 34, is then bent downward within a space 58 provided on the contact surface of the slider front part 34 and slider rear part 35 and is led into a groove 59 provided on the contact surface of the slider front part 34 and slider rear part 35. One electrode part 9 is sealed at the end with plastic 60 as shown in FIG. 8 within a groove 59. The other electrode part is pressed and connected at the end with a fastening pipe 62 as electrically connected with the front part of the cord part 10 within a space 61 provided on the contact surface of the slider front part 34 and slider rear part 35 from the groove 59 and is coated with a thermocontracting tube 63 for electric insulation on the periphery of the fastening pipe 62. Below the space 61, a clamp 64 is wound on the cord part 10 lest the cord part 10 should be pulled down.

FIG. 10 is a view showing a sheath 2 as combined with a mandolin 65 for closing the tip opening of the sheath 2 so that the above mentioned sheath 2 may smoothly enter the urethra.

As shown in FIGS. 11 to 14, the mandolin 65 has an outside diameter substantially equal to the inside diameter of the hollow tube part 2a of the sheath 2 and is formed of a tip part 67 formed to be circular near the tip, a gripping part 68 on the hand base side and a bar part 69 holding and connecting the above mentioned tip part 67 and gripping part 68. The sheath 2 is formed of the hollow tube part 2a and a sheath body 70.

A tapered part 73 to be fitted in a tapered hole 72 of an operating part connecting part 71 provided near the hand base of the sheath body 70 is provided near the tip part of the above mentioned gripping part 68. Connecting pins 74a projecting in the diametral direction are provided on both right and left sides. A positioning pin 74b projecting also in the diametral direction is provided on the lower side. They can be engaged respectively correspondingly with connecting grooves 75a and a positioning groove 75b formed in the operating part connecting part 71. The tip part 67, gripping part 68, bar part 69, connecting pins 74a and positioning pin 74b are integrally molded of such electric insulating material as plastic and can be made much more cheaply than in conventionally making them of a metal.

The hollow part 76 is provided as opened forward on the front end surface of the gripping part 68 so as to reduce the thickness of the tapered part 73. This means that retraction or the like for molding plastics can be prevented, the dimensional precision of the tapered part 73 can be improved and, in case the gripping part 68 is pushed into the operating part connecting part 71, the tapered part 73 of the gripping part 68 will contact the tapered hole 72 on the operating part contact part 71 side. The tapered part 73 will thus be able to be deflected in the inside diameter direction, therefore the sealing between the tapered hole 72 and tapered part 73 will be improved and the watertightness will be improved.

The sheath 2 is formed of the above mentioned hollow tube part 2a. The above mentioned sheath body part 70 is formed to be tubular and communicating with the hand base side of the hollow tube part 2a. A rotary cock 78 is rotatably loosely fitted to the outer peripheral surface on the tip side of the sheath body part 70. A cam groove sleeve 80 is connected to cover the outer peripheral surface on the hand base side of the sheath body part 70 and has cam grooves 79a formed to be bent for removably connecting the connecting pins 74a of the mandolin 65. A cover 81 covers the outer peripheral surface of the cam groove sleeve 80.

These hollow tube part 2a, sheath body part 70, rotary cock 78, cam groove sleeve 80 and cover 81 are all formed of plastic which is an electric insulating material.

The hollow tube path 2a having an outside diameter insertable into a body cavity is made of insulating material such as an epoxy resin heatproof enough against heat generated when resecting or coagulating an affected part by passing electricity through the electrode 5 inserted through the hollow tube path 2a and is extended so as to perfectly cover the optical sighting tube inserting part 11 of the operating part 3 including the electrode 5 in case the electrode 5 is fully pulled in on the hand base side.

On the outer periphery on the tip side of the sheath body part 70 fixed by bonding or the like on the hand base side of the hollow tube path 2a, a small diameter part 91, intermediate diameter part 87 and large diameter part 84 are formed so as to be larger in outside diameter in three steps from the tip side toward the middle part. An O-ring groove 83 is provided on the peripheral wall of the large diameter part 84. A water feeding hole 86 passing through the body space part 85a within the sheath body part 70 is provided on the peripheral wall of the intermediate diameter part 87. A snap fitting recess 90 is provided on peripheral wall of the small diameter part 91.

In the middle part of the outer peripheral wall of the rotary cock 78 formed to cover from the large diameter part 84 to the small diameter part 91 of the sheath body part 70, a lure lock female side mouthpiece 77 connecting a lure lock male side mouthpiece of a water feeding tube from a water feeding pump (not illustrated) is provided to project and a water feeding hole 93a is provided. In the inner peripheral part of the rotary cock 78, there are provided a first inner peripheral part 92 having substantially the same inside diameter as the diameter of the large diameter part 84 of the sheath body part 70 toward the tip side from the hand base side, covering the large diameter part 84 and intermediate diameter part 87 and having an opening 93b communicating with the above mentioned water feeding hole 93a. A second inner peripheral part 94 has substantially the same inside diameter as the diameter of the intermediate diameter part 87 and covers the hand base side of the small diameter part 91. A third inner peripheral part 88 has substantially the same inside diameter as the diameter of the small diameter part 91 and has a snap fitting projection in the position corresponding to the above mentioned snap fitting recess 90.

By engaging the snap fitting projection 89 with the snap fitting recess 90 of the sheath body part 70, the rotary cock 78 is rotatably and removably connected with the sheath body part 70.

A water feeding groove 95 is formed by the intermediate diameter part 87 and first inner peripheral part 92.

An O-ring groove 96 is formed by the small diameter part 91 and second inner peripheral part 94. O-rings 97 and 98 are fitted respectively in the O-ring groove 96 and the above mentioned O-ring groove 83 so as to lead the fluid from the water feeding hole 93a to the body space part 85a and to prevent water from leaking out of the water feeding groove 95.

Figure 15:
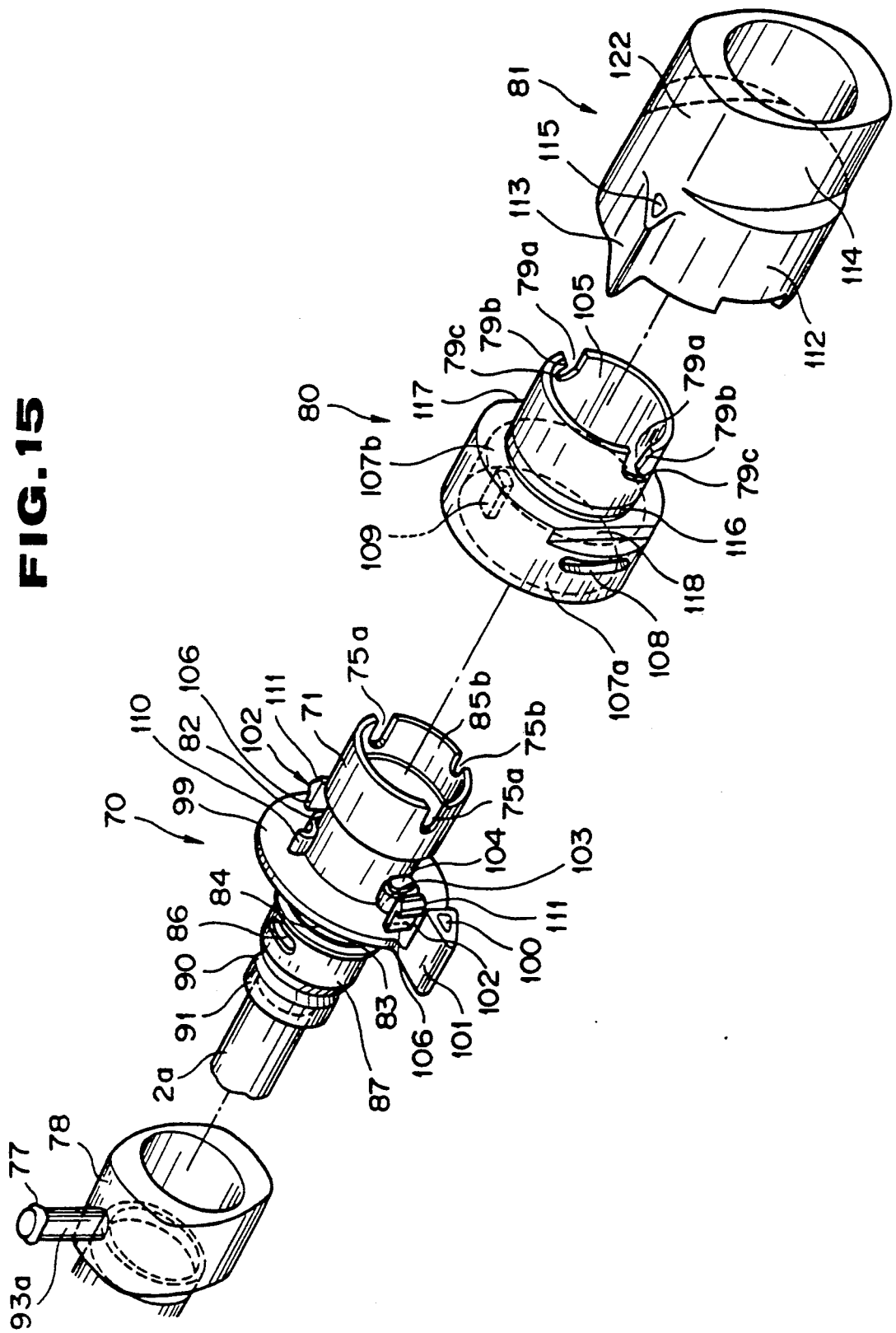

As shown in FIG. 15, in the sectioned view in the direction at right angles with the center axis of the rotary cock 78, the outer peripheral part of the rotary cock 78 is formed to be substantially an ellipse, short in diameter in the horizontal direction and long in diameter in the vertical direction. As the outer peripheral part of the rotary cock 78 is thus formed to be substantially an ellipse, the outer peripheral part is easy to hold and can be made easy to rotate. Conventionally, as the rotary cock is not circular in the cross-section in the direction at right angles with the center axis when rotating the rotary cock with respect to the sheath body, as there is no place to place the operator's fingers on the outer peripheral part, the rotary cock will be hard to rotate or the operator's fingers will be placed on the lure lock cock female side mouthpiece which will be thus rotated. There has been a problem that a large load will be applied to the root of the lure lock cock female side mouthpiece to break the mouthpiece. The present invention solves this problem.

As described above, as the rotary cock 78 is removably connected by engaging the snap fitting projection 89 with the snap fitting recess 90, for example, in case the rotary cock 78 or lure lock female side mouthpiece 77 is broken during use or the O-ring 97 or 98 is broken, it will be able to be very easily replaced or assembled.

A flange 99 continuously protruding in a direction at right angles with the center axis is provided on the hand base side of the large diameter part 84 of the sheath body part 70. A finger hanging grip 101 projecting in the outer peripheral direction and having a hollow hole 100 projected on the hand base side is provided on a part of the outer periphery of the flange 99.

The hand base side end surface of the rotary cock 78 is in contact with the tip side wall surface of the flange 99 and the outside diameter of the flange 99 is made somewhat larger than the outside diameter of the rotary cock 78.

Near the outer periphery of the hand base side wall surface of the flange 99, snap fitting pawls 102 projected substantially parallelly with the center axis and a spring pin 104 for fitting a winding part 103 provided at one end of a plate spring 82 are provided to project.

The hand base side outer periphery continuing to the flange 99 of the sheath body part 70 is formed to be of a small diameter substantially the same as the diameter of the small diameter part 91 and forms a space containing the plate spring 82. The operating part connecting part 71 opened at the hand base side end containing the connecting pins 74a and positioning pin 74b of the mandolin 65 and having the connecting grooves 75a and positioning groove 75b formed parallelly with the center axis is provided on the hand base side.

The central space part 85b formed within the above mentioned operating part connecting part 71 externally fits the outer peripheral part 85c provided with the connecting pins 74a and positioning pin 74b of the gripping part 68 of the mandolin 65 and has an inside diameter somewhat larger than the diameter of this outer peripheral part 85c. The above mentioned tapered hole 72 corresponding to the tapered part 73 of the mandolin 65 is provided as continued to this central space part 85b. Following it, there is provided the above mentioned body space part 85a having an inside diameter which is large enough to be able to insert and pass the optical sighting tube inserting part 11 of the operating part 3 containing the electrode 5 and loop 52. The above mentioned body space part 85a is further provided into the hollow tube part 2a near the tip so that there may be no step catching on the loop 52 or the like in case it is inserted into the hollow tube part 2a from within the operating part connecting part 71.

The above mentioned cam groove sleeve 80 is provided with a tubular cam part 105 having the same inside diameter as the diameter of the outer periphery of the operating part connecting part 71 and provided with a cam groove 79a. A spring cover part 107 has the same outside diameter as the outside diameter of the flange 99 and has an inside diameter equal to or somewhat larger than the outside diameter of the cover supporting part 106 on the root side of the snap fitting pawl 102. A wall part 107b is vertical to the center axis connecting the cam part 105 and spring cover part 107. Near the side wall 107b which is the peripheral wall of the spring cover part 107a, there are provided symmetrically with the center axis of the spring cover part 107a two snap fitting holes 108 formed to be substantially elliptic so as to have the major diameter in the peripheral direction through the inner periphery from the outer periphery. On the tip side of the wall part 107b within the cam groove sleeve 80, the spring pin 109 is provided to project on the sheath body part 70 side substantially parallelly with the center axis.

The sheath body part 70, cam groove sleeve 80 and plate spring 82 are fixed by fitting the winding part 103 at one end of the plate spring 82 into the spring pin 104 of the sheath body part 70 and engaging the hook part 110 provided at the other end of the plate spring 82 with the spring pin 109 of the cam groove sleeve 80. In this case, the engaging parts 111 projecting in the diametral direction from the outer peripheral surface of the spring cover supporting parts 106 at the tips of the snap fitting pawls 102 of the sheath body part 70 will be engaged and connected with the snap fitting holes 108 of the cam groove sleeve 80.

As the plate spring 82, the spring pin 104 of the sheath body part 70 and the spring pin 109 of the cam groove sleeve 80 are formed as mentioned above, there are reflects that the assembly, removal and replacement can be made very easily without screwing, bonding and fixing the plate spring at one end to the sheath body as in the past.

Figure 14:
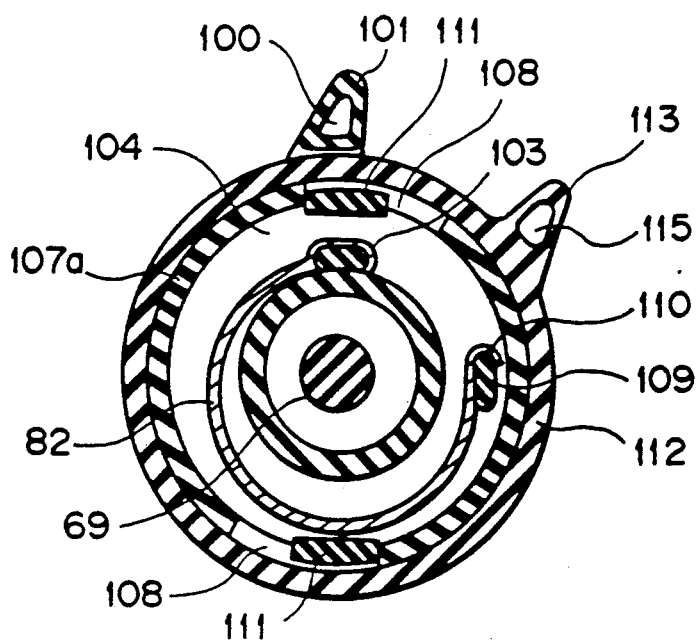

As shown in FIG. 14, the plate spring 82 is energized to rotate the cam groove sleeve 80 clockwise with respect to the sheath body part 70 and the rotation of the cam groove sleeve 80 is regulated by the contact of the engaging parts 111 of the snap fitting pawls 102 with the end surfaces in the peripheral direction (major diameter direction) of the snap fitting holes 108. Even if the plate spring 82 is energized to rotate the spring cover part 107a counterclockwise with respect to the sheath body part 70, the engaging parts 111 will contact the other end surfaces in the peripheral direction (major diameter direction) of the snap fitting holes 108 to regulate the rotation of the spring cover part 107a.

The spring cover 107a rotates in the range of the major diameter of the snap fitting hole 108 and the snap fitting pawl 102 and snap fitting hole 108 snap fit fix the sheath body part 70 and cam groove sleeve 80 and at the same time act to regulate the rotation of the cam groove sleeve 80.

As described above, the sheath body part 70 and cam groove sleeve 80 are connected by the engagement of the snap fitting pawls 102 with the snap fitting holes 108. In this connection, as the step made by the engaging part 111 of the snap fitting pawl 102 and the spring cover supporting part 106 engages with the edge of the snap fitting hole 108, the sheath body part 70 and cam groove sleeve 80 can not be easily separated and removed in the central axial direction.

However, when the cover 81 is removed from the cam groove sleeve 80, for example, if a small diameter tool such as a screw driver is inserted into the snap fitting holes 108 and the engaging parts 111 of the snap fitting pawls 102 are pushed in the inside diameter direction, the engagement will be able to be released and the sheath body part 70 and cam groove sleeve 80 will be able to be easily removed.

Figure 13:
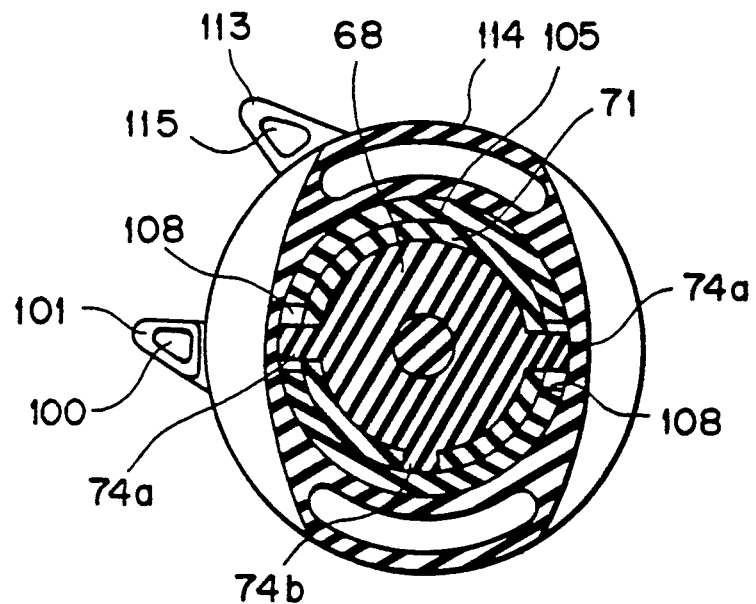

The above mentioned cover 81 is formed of a snap fitting cover part 112 having the same inside diameter as the outside diameter of the flange 99 of the sheath body part 70 and the outside diameter of the spring cover part 107a of the cam groove sleeve 80, a finger hanging grip part 113 projecting in the outside diameter direction from the peripheral wall of the snap fitting cover 112 and having a hollow hole 115 and a cam groove cover part 114 having the same inside diameter as the outside diameter of the cam part 105, having a substantially elliptic cross-section as is shown in FIG. 13 in a direction at right angles with the center axis and provided on the hand base side of the snap fitting cover part 112.

On the outer periphery near the wall part 107b of the above mentioned cam part 105, a snap fitting projection 116 is annularly provided and a snap fitting recess 121 is provided in the inside diameter of the cam groove cover part 114 of the cover 81 corresponding to the projection 116. At the hand base side end of the spring cover part 107a, a large incision 117 and a small incision 118 of an incised depth smaller than of the large incision 117 are provided in the positions symmetrical with the center axis. On the inner peripheral wall of the snap fitting cover part 112, a large projection 119 is provided in the position corresponding to the above mentioned large incision 117 and a small projection 120 is provided in the position corresponding to the above mentioned small incision 118.

When the above mentioned snap fitting projection 116 is engaged with the snap fitting recess 121, they will be removably connected with each other. When the large projection 119 is engaged with the large incision 117 and the small projection 120 is engaged with the small incision 118, they will be able to be very easily removably connected with each other without rotating the cam groove sleeve 80 and cover 81 with each other or without mistaking the rotating position in assembling.

As shown in FIG. 1, when the sheath 2 and operating part 3 are connected with each other, the cam groove cover part 114 will have its upper side outside diameter part substantially on the same level as a finger placing part 123 provided parallelly with the center axis of the tip side from near the root of the upper finger hanger 26 of the operating part body 13. Thus, the defect can be solved when the operator places the forefinger on the upper finger hanger 26 and finger placing part 123, the middle finger, third finger and little finger on the lower finger hanger 25 and the thumb on the thumb hanger 41, in the conventional resectoscope, since a step is made by the level difference between the upper side outside diameter part 122 and finger placing part 123, the forefinger will fall down the step during the operation and the operation will be difficult.

Figure 16:
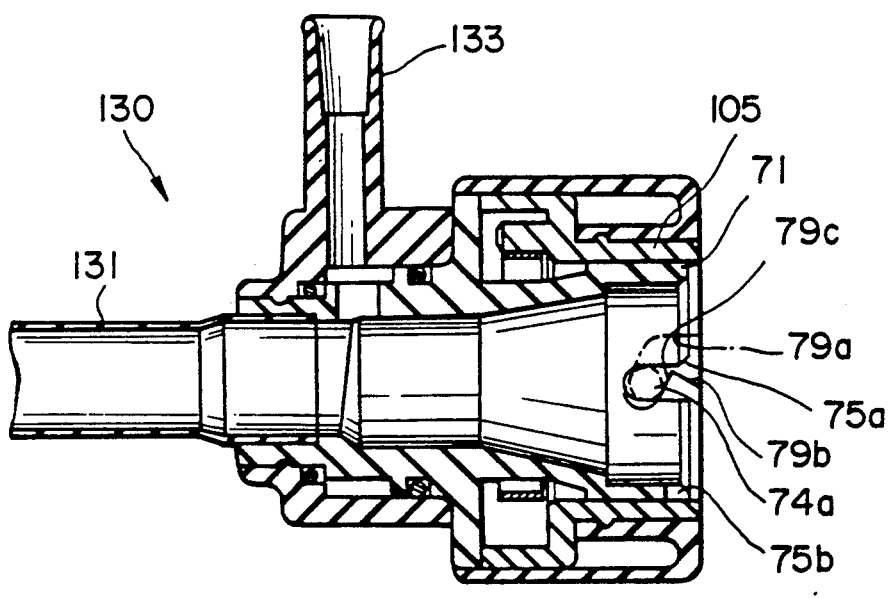

The cam groove sleeve 80 is rotated clockwise by the energizing force of the plate spring 82 and, as shown in FIG. 16, the cam grooves 79a are always kept substantially coinciding with the connecting grooves 75a of the operating part connecting part 71 in the deep part.

As shown in FIG. 16, one side surface forming the cam groove 79a consists of two slopes 79b and 79c projecting toward the other side surface side so as to reduce the width of the cam groove 79a. These two slopes 79b and 79c incline in directions reverse to each other and project so as to reduce (clog) the groove width near the inlet of the connecting groove 75a. Therefore, when the mandolin 65 is inserted into the operating part connecting part 71 from the tip part 67 side, the connecting pin 74a of the mandolin 65 will contact the above mentioned slope 79b. When the above mentioned slope 79b is pushed against the energizing force of the plate spring 82, the cam groove sleeve 80 will rotate and the connecting pin 74a will be able to be pushed over the slope 79b into the deep sides of the connecting groove 75a and cam groove 79a.

When the connecting pin 74a is thus pushed over the slope 79b, the cam groove sleeve 80 will be rotated clockwise by the energizing force of the plate spring 82 and the connecting pin 74a will slide on the other slope 79c and will be contained in the deepest parts of the connecting groove 75a and cam groove 79a.

In this state, the connecting pin 74a will contact the sharp slope 79c and will be kept locked to be prevented from being pulled out rearward. In this state, the tapered part 73 of the gripping part 68 of the mandolin 65 and the tapered hole 72 of the sheath body part 70 will be in close contact with each other to be kept watertight.

When removing the fitted mandolin 65, when the fingers are placed to grip the finger hanging grip 10 of the sheath body part 70 and the finger hanging grip 113 of the cover 81 connected to the cam groove sleeve 80 and the cam groove sleeve 80 is rotated counterclockwise against the energizing force of the plate spring 82, the slopes 79c locking the connecting pins 74a on the rear sides of the connecting pins 74a will rotate and retreat together with the cam groove sleeve 80. The locking will be released and the mandolin 65 will be able to be simply pulled out.

When using the resectoscope apparatus formed as mentioned above, as shown in FIG. 10, the mandolin 65 is inserted and connected to the sheath 2, the tip part 67 of the mandolin 65 and the hollow tube part 2a of the sheath 2 are inserted into the body cavity of the patient, then the mandolin 65 is pulled out of the sheath 2. Instead, if the operating part 3 and optical sighting tube 4 are inserted and connected to the sheath 2 as shown in FIG. 1, the operator's thumb is put into the space formed by the thumb hanger 41 and the slider rear part 35, the forefinger is placed on the upper finger hanger 26 and finger placing part 123, the middle finger, third finger and little finger are placed on the lower finger hanger 25 and the slider part 12 is advanced.

The electrode 5 fixed to the slider part 12 will advance with the advance of the slider part 12 and the loop 52 provided at the front end of the electrode 5 will project from the front end of the hollow tube part 2 of the sheath 2. While observing with the optical sighting tube 4, the affected part is positioned between the loop 52 and the front end of the hollow tube part 2a and the electrode is fed with a high frequency current from a high frequency current source (not illustrated). Then the pushing of the slider part is released. The slider part 12 will be retreated rearward by the energizing force of the coil spring 28, the above mentioned loop will also retreat with it and therefore the above mentioned affected part will be able to be inserted between the front end of the hollow tube part 2a and the loop 52. The loop 52 is fed with the high frequency current and can burn off the inserted affected part.

As in the above, in this embodiment, the tip side of the electrode 5 through which a high frequency current is passed is enclosed with the hollow tube part 2a of the sheath 2 formed of an electric insulating material, is continuously enclosed toward the hand base side will the sheath body part 70 formed of the same electric insulating material, is further passed through the sheath connecting part 19 formed of the electric insulating material of the operating part 3, is covered with the cover 22 formed of the same electric insulating material, is inserted by the slider front part 34 and slider rear part 35 formed also of the electric insulating material and is connected to the cord part 10 within the slider part 12. That is to say, the electrode 5 is enclosed or covered over the entire length with parts formed of an electric insulating material of the sheath 2 and operating part 3 such as the hollow tube part 2a, sheath body part 70, sheath connecting part 19, cover 22 and slider part 12.

Therefore, the patient and operator can be perfectly electrically separated from the electrode through which a high frequency current flows. In case the insulating coating material of the electrode is broken, the patient and operator will be able to be prevented from being burned or electrically shocked by the current flowing through the operating part and the conductive members of the sheath and the affected part will be able to be safely operated on.

In this embodiment, as an electric insulating material, plastic is used but ceramic as, for example, glass ceramic made by depositing mica (fluorine gold mica) may be also used.

FIGS. 17 to 20 show the second embodiment of the present invention.

In this embodiment, in the resectoscope apparatus 1 of the first embodiment, the formation of the sheath 2 is modified but the operating part 3, optical sighting tube 4 and mandolin 65 are the same as in the first embodiment.

Figure 17:
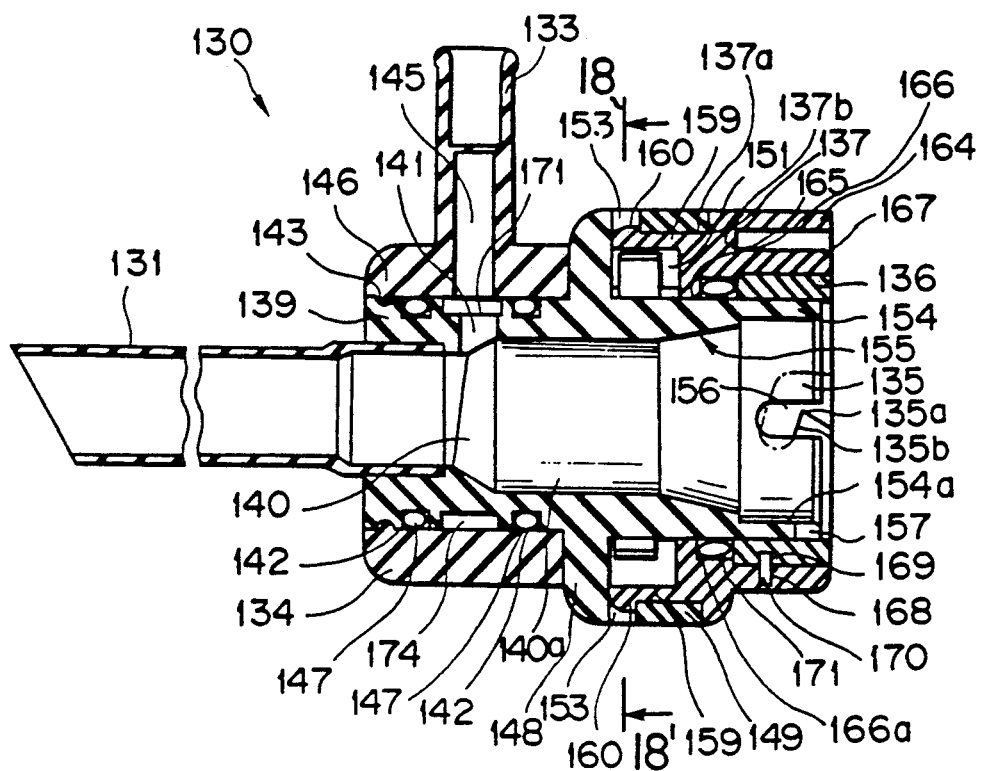
Figure 18:
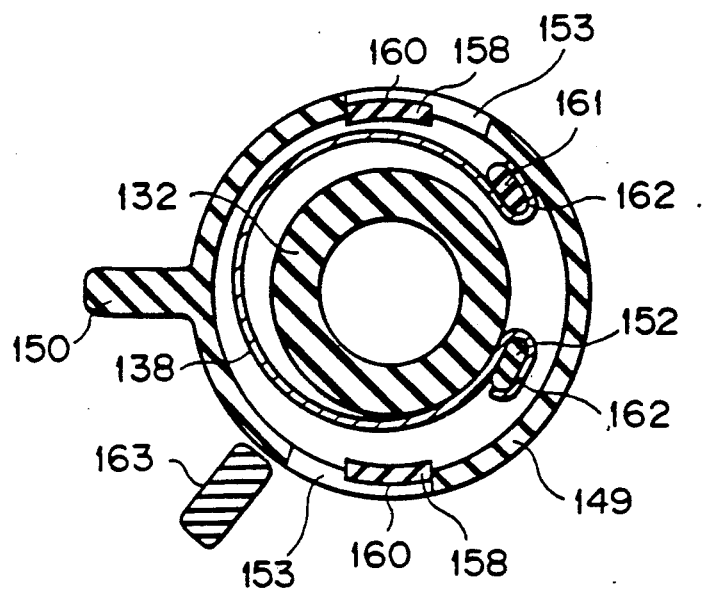
Figure 21:
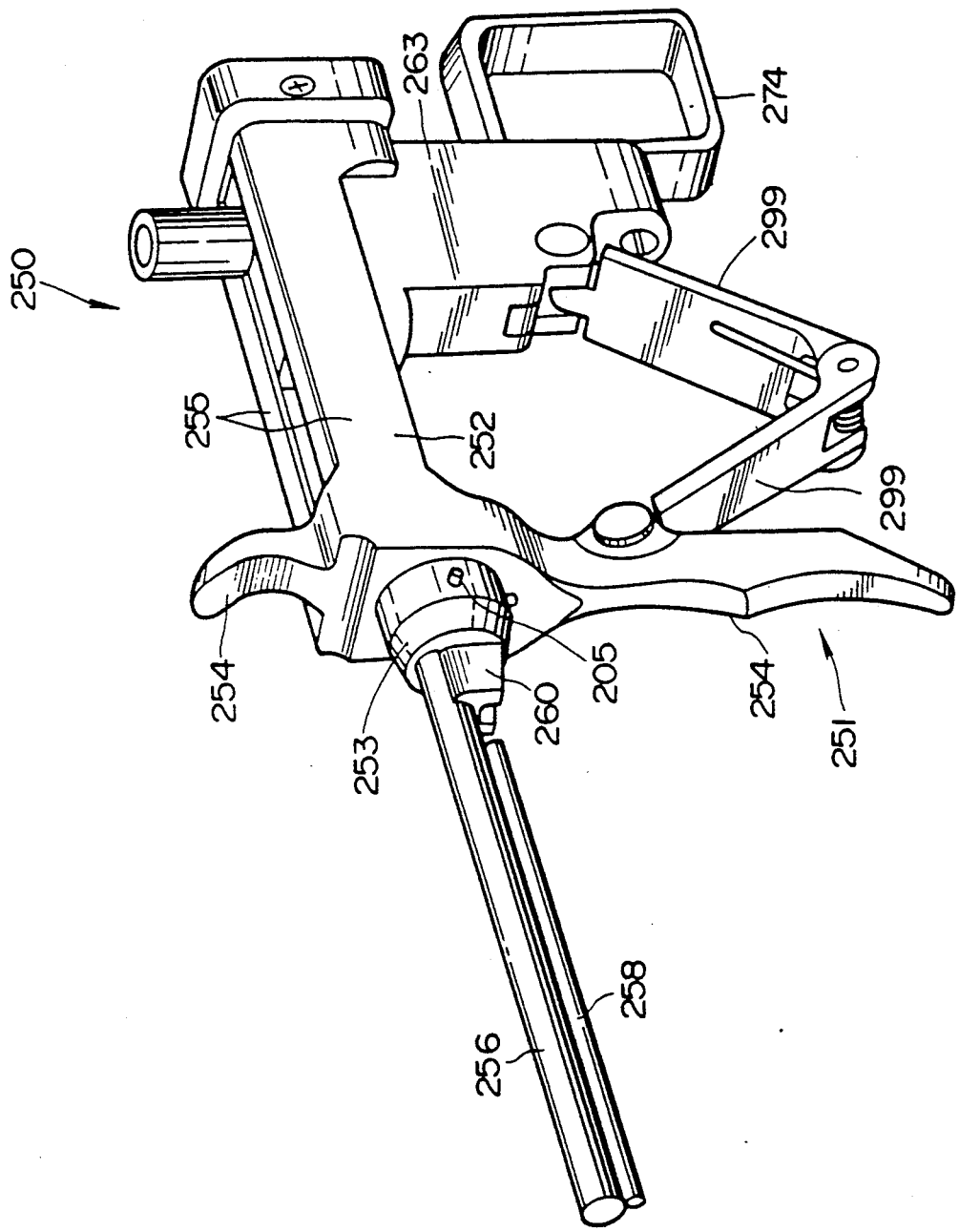
FIGS. 21 to 29 relate to the third embodiment of the present invention.

As shown in FIGS. 17 to 19, a sheath 130 comprises a hollow tube part 131 substantially the same as of the sheath 2 of the first embodiment. A tubularly formed sheath body part 132 communicates with the hollow tube part 131. A rotary cock 134 is connected to cover the outer peripheral surface on the tip side of the sheath body part 132 and has a lure locking female side mouthpiece 133 for connecting a lure locking male side mouthpiece of a water feeding tube (not illustrated). A cam groove sleeve 136 has cam grooves 135 formed to be bent to push in connecting pins 74a of the mandolin 65. A cover 137 is contained and connected on the hand base side of the cam groove sleeve 136 and is connected to cover the outer peripheral surface on the hand base side of the sheath body part 132. The same as in the first embodiment, the sheath body part 132, rotary cock 134, cam groove sleeve 136 and cover 137 are formed of electric insulating material such as a synthetic resin.

The hollow tube part 131, having an outside diameter insertable into a body cavity, is made of a heatproof resin having a sufficient heatproofness against heat generated when resecting or coagulating an affected part by passing an electric current through the electrode 5 inserted into the hollow tube part 131. For example, the resin can be polyether imide, polyimide or polyacid imide and the resin is extended to completely cover the optical sighting tube inserting part 11 of the operating part 3 including the electrode 5 when the electrode 5 is fully pulled in on the hand base side.

A rotary cock connecting part 139 is fixed as by bonding on the hand base side of the hollow tube part 131 and has the same outside diameter from the tip of the outer peripheral wall of the sheath body part 132 to near the middle. On the outer periphery of the connecting part 139, there are provided in the order mentioned from the near tip side a snap fitting recess 143, O-ring groove 142, water feeding hole 141 passing through the body space part 140, water feeding groove 174 on the periphery of the water feeding hole 141 and O-ring groove 142 on the hand base side of the water feeding groove 174. The space part 144 of the rotary cock 134 has substantially the same inside diameter as the outside diameter of the rotary cock connecting part 139 and is provided near the middle with a water feeding hole 145 communicating with the lure locking female side mouthpiece 133 and near the tip with a snap fitting projection 146 in the position corresponding to the snap fitting recess 143 of the rotary cock connecting part 139. The rotary cock 134 is removably connected to the sheath body part 132 by engaging the snap fitting projection 146 with the snap fitting recess 143.

O-rings 147 are fitted respectively in the O-ring grooves 142 so that the fluid from the water feeding hole 145 may be led to the body space part 140 through the water feeding hole 141 and the water leak from the water feeding groove 174 may be prevented.

Thus, the same as in the sheath 2 of the first embodiment, there are effects that, in case, for example, the rotary cock 134 or lure locking female side mouthpiece 133 is broken during use or the O-ring 147 is broken, it will be easily replaced and the assembling will be easy.

Near the middle of the sheath body part 132, a flange 148 is projected in a direction at right angles with the center axis as continued to the hand base side of the rotary cock connecting part 139. A snap fitting cover part 149 is formed to be cylindrical to the hand base side from the outer peripheral part of the flange 148. A finger hanging grip 150 is projected in the diametral direction from the outer peripheral wall of the snap fitting cover part 149. The outside diameters of the outer periphery of the flange 148 and the outer periphery of the snap fitting cover part 149 are somewhat larger than the outside diameter of the rotary cock 134. The hand base side end surface of the rotary cock 134 contacts the tip side wall surface of the flange 148.

On the hand base side wall surface of the flange 148 of the space part 151 of the snap fitting cover part 149, a spring pin 152 is provided to project substantially parallelly with the center axis. Snap fitting holes 153 pass through the outer peripheral wall of the snap fitting cover part 149 to the space part 151, are formed to be substantially ellipses having the major diameters in the peripheral direction and are provided to be symmetrical with each other with respect to the center axis.

The hand base side outer periphery continued from the space part 151 of the snap fitting cover part 149 of the sheath body part 132 to the hand base side end surface has substantially the same outside diameter as the rotary cock connecting part 139. Near the hand base side, the operating part connecting part 154 has connecting grooves 156 and a positioning groove 157 containing the connecting pins 74a and positioning pin 74b of the mandolin 65, opened at the hand base side end and formed to be parallel with the center axis.

The body space part 140 of the sheath body part 132 has on the hand base side a space part 154a of an inside diameter somewhat larger than the diameter of the outer peripheral part 85c of the mandolin 65, is provided following it with a tapered part 155 corresponding to the tapered part 73 of the mandolin 65 and is provided following it with a middle space part 140 having an inside diameter which can insert and pass with a sufficient space the optical sighting tube inserting part 11 of the operating part 3 including the electrode 5 and loop 52 so that there may be no catching step near the tip in the case of inserting the loop 52 or the like into the hollow tube part 131 from within the operating part connecting part 154.

On the outer periphery on the tip side of the cover 137, there is a cover connecting part 137a having the same outside diameter as the inside diameter of the snap fitting cover part 149 and, from the tip side end surface of the cover 137, snap fitting pawls 158 formed of snap fitting cover supporting parts 159 having the same outside diameter as the diameter of the outer periphery of the cover connecting part 137a and engaging parts 160 projecting in the diametral direction from the tips of the supporting parts 159 are provided to project in two places symmetrically with respect to the center axis. A spring pin 161 projecting in the direction of the sheath body 132 is provided parallelly with the center axis in the position rather near to the inside diameter from the outer periphery of the tip side end surface of the cover 137.

The inner peripheral part of the cover 137 is formed to be larger in inside diameter in three steps from the tip side to the hand base side. The first inner peripheral part 165 on the tip side has the same inside diameter as the diameter of the outer periphery of the operating part connecting part 154. The second inner peripheral part 166 near the middle is of an inside diameter somewhat larger than the diameter of the first inner peripheral part 165. The third inner peripheral part 167 on the hand base side has an inside diameter larger than the diameter of the second inner peripheral part 166 and has a pin hole 168 passing in the diametral direction from the outer periphery for inserting the pin 170 on the tip side from the middle of the lower side of the third inner peripheral part 167.

A butting flange 137b, having the same outside diameter as the diameter of the outer periphery of the snap fitting cover part 149 for contacting the hand base side end surface of the snap fitting cover part 149, is provided on the hand base side of the cover connecting part 137a on the outer peripheral part of the cover 137. An arcuate protruding part 164, protruding like a visor on the hand base side as continued from the butting flange 137b, is provided from near the middle of the upper part of the outer periphery of this cover 137 to the hand base side end surface. A finger hanging grip part 163 projecting in the diametral direction is provided from the butting flange 137b to near the hand base side on the obliquely lower left surface on which the protruding part 164 is not provided on the outer peripheral wall on the hand base side of the cover 137.

The above mentioned cam groove sleeve 136 is of the same inside diameter as the diameter of the outer periphery of the operating part connecting part 154 and is of the same outside diameter as the inside diameter of the third inner peripheral part 167 of the cover 137. The above mentioned cam grooves 135, formed as bent on the hand base side end surface of the cam groove sleeve 136, are provided symmetrically on the right and left with respect to the center axis. On the lower side surface, a pin hole 169 for inserting a pin 170 is provided in the diametral direction in the position corresponding to the pin hole 168 of the third inner peripheral part 167 of the cover 137.

The cam groove sleeve 136 is inserted and contained in the third inner peripheral part 167 of the cover 137 and is fixed and connected to the cover 137 by positioning the pin holes 168 and 169, inserting the pin 170 and such means as bonding.

The cover 137, made integral with the cam groove sleeve 136 as mentioned above, is snap fit connected with the sheath body part 132 by engaging the engaging parts 160 of the snap fitting pawls 158 of the cover 137 respectively with the snap fitting holes 153 of the snap fitting cover part 149 of the sheath body part 132.

The plate spring 138 has hook parts 162 formed like hooks at both ends and can be easily fitted by putting the plate spring 138 into the space part 151 of the snap fitting cover part 149 and hanging the hook parts 162 respectively on the spring pin 152 of the sheath body part 132 and the spring pin 161 of the cover 137. As shown in FIGS. 17 and 18, the cover 137 is always energized counterclockwise with respect to the sheath body part 132.

An O-ring 171 is fitted in the groove 166a formed by the step between the first inner peripheral part 165 and second inner peripheral part 166 of the cover 137 and the tip side end surface of the cam groove sleeve 136 so that liquid, such as water coming through the clearance between the outer periphery of the cam groove sleeve 136 and the third inner peripheral part 167 from the cam groove 135, may be prevented from leaking into the space part 151 of the snap fitting cover part 149.

The protruding part 164 provided on the cover 137 is formed so that the upper surface may be substantially on the same level as the finger placing part 123 of the operating part 3 in case the sheath 130 and operating part 3 are combined with each other.

Thus, the same as in the first embodiment, the defect can be solved that, in order to hold the operating part 3, the operator places the forefinger on the upper finger hanger 26 and finger placing part 123, the middle finger, third finger and little finger on the lower finger hanger 25 and the thumb on the thumb hanger 41, in the conventional resectoscope apparatus, as a step is formed by the level difference between the protruding part 164 and finger placing part 123, the forefinger will fall down the step during the operation and the operation will be difficult.

Recesses 172 are provided on the sides of the outer peripheral surface of the rotary cock 134 which can be easily rotated by placing the fingers on these recesses 172.

These recesses 172 may be knurled 173 as in FIG. 20. The outer periphery of the rotary cock 134 may be otherwise formed so as to be easy to place the fingers on.

The same as in the first embodiment, the sheath body part 132 and cover 137 are connected with each other by the engagement of the snap fitting pawls 158 with the snap fitting holes 153. In this connection, as the step formed by the engaging part 160 of the snap fitting pawl 158 and the snap fitting cover supporting part 159 is engaged with the edge of the snap fitting hole 153, even if the sheath body part 132 and cover 137 are simply separated from each other in the center axial direction, they will not be able to be easily removed.

However, if a small diameter tool as, for example, a screw driver is inserted into the snap fitting holes 153 and the engaging parts 160 of the snap fitting pawls 158 are pushed in the inside diameter direction, the snap fit will be able to be released and the sheath body part 132 and cover 137 will be able to be easily removed.

Thus, as the sheath body part 132 and cover 137 can be easily removably connected with each other by the snap fitting, the plate spring 138 and others can be very easily replaced. It is needless to say that the assembling is very easy.

As shown in FIG. 18, the plate spring 138 energizes the cover 137 to rotate counterclockwise with respect to the sheath body part 132 and the rotation of the cover 137 is regulated by the contact of the engaging parts 160 of the snap fitting pawls 158 with the end surfaces on one side in the peripheral direction (major diameter direction) of the substantially elliptic snap fitting holes 153. Even if the cover 137 is rotated counterclockwise with respect to the sheath body part 132 against the energizing force of the plate spring 138, the engaging parts 160 will contact the end surfaces on the other side in the peripheral direction (major diameter direction) of the snap fitting holes 153 to regulate the rotation of the cover 137.

That is, the cover 137 rotates in the range of the major diameter of the snap fitting hole 153. The snap fitting pawl 158 and snap fitting hole 153 snap fit fix the sheath body part 132 and cover 137 and at the same time act to regulate the rotation of the cover 137 with respect to the sheath body part 132.

By being integrally connected with the cover 137, the cam groove sleeve 136 is energized counterclockwise by the plate spring 138. In this case, as shown in FIG. 17, the cam grooves 135 will substantially coincide with the connecting grooves 156 of the 15 operating part connecting part 154 in the deep parts.

As shown in FIG. 17, one side surface forming the cam groove 135 consists of two slopes 135a and 135b projecting toward the other side surface side so as to reduce the width of the cam groove 135.

These two slopes 135a and 135b incline in directions reverse to each other to reduce (clog) the groove width near the inlet of the connecting groove 156. Therefore, when the mandolin 65 is inserted into the operating part connecting part 154 from the tip part 67 side, the connecting pin 74a of the mandolin 65 will contact the above mentioned slope 135a.

When the above mentioned slope 135 is pushed against the energizing force of the plate spring 138, the cam groove sleeve 136 will rotate as operatively connected to the cover 137 and the connecting pins 74a will be able to be pushed into the deep part sides of the connecting grooves 156 and cam grooves 135 over the slopes 135a.

When the connecting pins 74a pass over the slopes 135a by this pushing in, by the energizing force of the plate spring 138, the cam groove sleeve 136 will be rotated clockwise as operatively connected with the cover 137 and the connecting pins 74a will slide on the other slopes 135b and will be contained in the deepest parts of the connecting grooves 156 and cam grooves 135.

In this state, the connecting pins 74a will contact the sharp slopes 135b and will be kept locked to be prevented from being pulled out rearward. In this state, the tapered part 73 of the gripping part 68 of the mandolin 65 and the tapered part 155 of the sheath body part 132 will be in close contact with each other to be kept watertight.

When the fitted mandolin 65 is to be removed, when the fingers are placed on the finger hanging grip 150 of the sheath body part 132 and the finger hanging grip part 163 of the cover 137 connected to the cam groove sleeve 136 to grip them and the cam groove sleeve 136 is rotated clockwise as operatively connected with the cover 137 against the energizing force of the plate spring 138, the slopes 135b locking the connecting pins 74a on the rear side of the connecting pins 74a will rotate and retreat together with the cam groove sleeve 136, the locking will be released and the mandolin 65 will be able to be simply pulled out.

The operating part 3 can be also connected to and pulled out of the sheath 130 the same as in the above.

The other formations, operations and effects are the same as in the first embodiment.

FIGS. 21 to 29 show the third embodiment of the present invention.

In this embodiment, an inner tube 202 of a hollow tube part of a sheath 200 and a slider 263 of an operating part 251 are formed of an electric insulating material such as plastic.

A body 252 of the operating part 251 is made integral with a sheath connecting part 253, finger hanger 254 and reinforcing part 255 as a cover part extended rearward of this finger hanger 254 and is formed of an electric insulating material such as plastic.

A resectoscope apparatus 250 of this embodiment comprises a sheath 200, an operating part 251 connected and fixed to the rear end of the sheath 200, an optical sighting tube 4 inserted from the rear of the operating part 251 and an electrode 203 inserted into the sheath 200 and connected to the operating part 251.

The body 252 of the above mentioned operating part 251 is provided in the front part with a sheath connecting part 253 removably connecting the above mentioned sheath 200, having on the outer periphery connecting pins 205 made of a metal to project on the right and left in the horizontal direction and provided with a guide tube 256 to be inserted in the front part through the sheath 200. The guide tube 256 is extended rearward through the sheath connecting part 253. A finger hanger 254 is provided to project in the vertical direction of the sheath connecting part 253. In the rear of the finger hanger 254, reinforcing parts 255 are extended as inserting and enclosing the above mentioned guide tube 256 and slidably holding the slider 263. This guide tube 256 is coated with an insulating pipe 257 formed of an electric insulating material such as plastic in the part projected between the reinforcing parts 255. Further, the guide tube 256 forward of the sheath connecting part 253 is parallelly provided with an electrode inserting tube 258.

The above mentioned sheath connecting part 253 is provided with an electrode inserting hole 259. A guide 260 leading the electrode 203 having passed through the electrode inserting tube 258 into the electrode inserting hole 259 is formed in front of this electrode inserting hole 259. An O-ring 261 keeping the watertightness at the time of inserting the electrode 203 is fixed by an O-ring presser 262 internally fitted as by snap fitting to the inner peripheral wall in the rear part of the electrode inserting hole 259.

Figure 24:
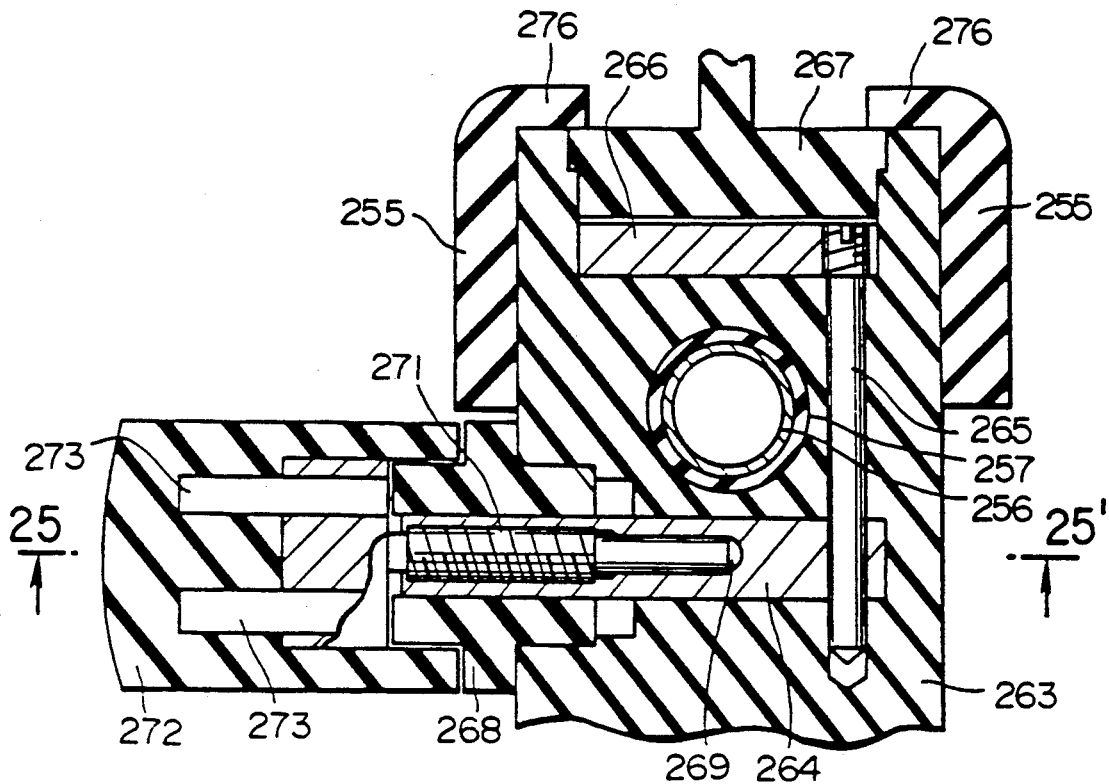
Figure 23:
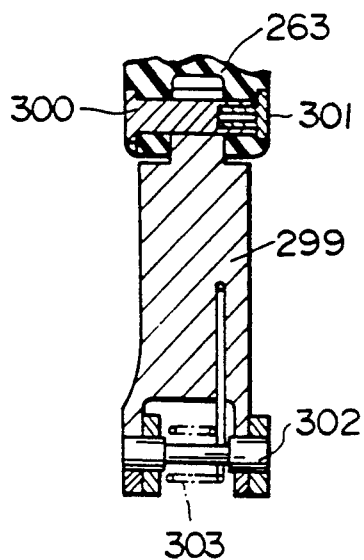
Figure 25:
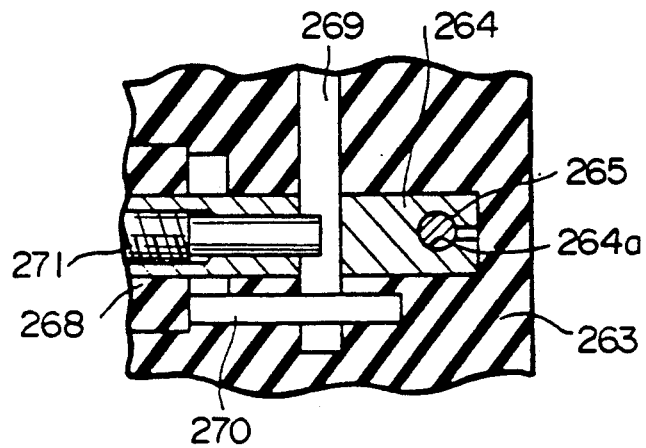

The insulating pipe 257 coating the above mentioned guide tube 256 is inserted through a guide tube inserting hole 275 provided in the slider 263 formed of an insulating material so that the slider 263 may be slidable forward and rearward. A columnar electrode receptacle 264 is inserted from the side as shown in FIG. 24 into the slider 263. The electrode receptacle 264 is provided in the tip part with a slit hole 264a provided with a slit. The electrode receptacle 264 is fixed to the slider 263 by pressing an elongate fixing pin 265 inserted from the upper part of the slider 263 into this slit hole 264. A screw part is provided in the head part of the fixing pin 265 and is screwed into an electrode cord connecting part 266 secured to the upper part of the slider 263 so that the electrode receptacle 264 and electrode cord connecting part 266 may be electrically connected with each other. The electrode cord connecting part 266 is prevented by a cap 267 made of an electric insulating material from being exposed.

An electrode inserting hole 269 passing through the above mentioned electrode receptacle 264 is provided on the front end surface of the above mentioned slider 263. A positioning pin 270 butting and positioning the end part of the electrode 203 inserted through this electrode inserting hole 269 is provided in the rear end part of this electrode inserting hole 269. A set screw 271 is screwed in the center axis of the electrode receptacle 264. The rear end part 204 of the electrode 203 is fastened and fixed with the tip part of this set screw 271. A grip 272 formed of an insulating material is secured to the head part of this set screw 271 and a pin 273 is inserted to reinforce the securing part. A cap 268, formed of an electric insulating material, is provided between the grip 272 of the above mentioned electrode receptacle 264 and the slider 263.

A finger hanging ring 274 formed of plastic or the like is rotatably provided by snap fitting in the lower part of the slider 263.

The distance between the reinforcing parts 255 is made somewhat larger than the width of the slider 263 and, as shown in FIG. 24, ribs 276 are formed by bending the upper parts to increase the bending rigidity.

An optical sighting tube inserting hole 278 inserting the above mentioned insulating pipe 257 is provided in an optical sighting tube connecting member 277 formed of metal such as stainless steel. The optical sighting tube 4 is to be inserted into the optical sighting tube inserting hole 278 from the rear. An O-ring 279, for keeping the watertightness at the time of inserting the optical sighting tube 4, is fixed with a nut 280 on the inner peripheral surface of the inserting hole 278. An O-ring 281 keeping the watertightness between the above mentioned insulating pipe 257 and the inserting hole 278 is provided.

Figure 26:
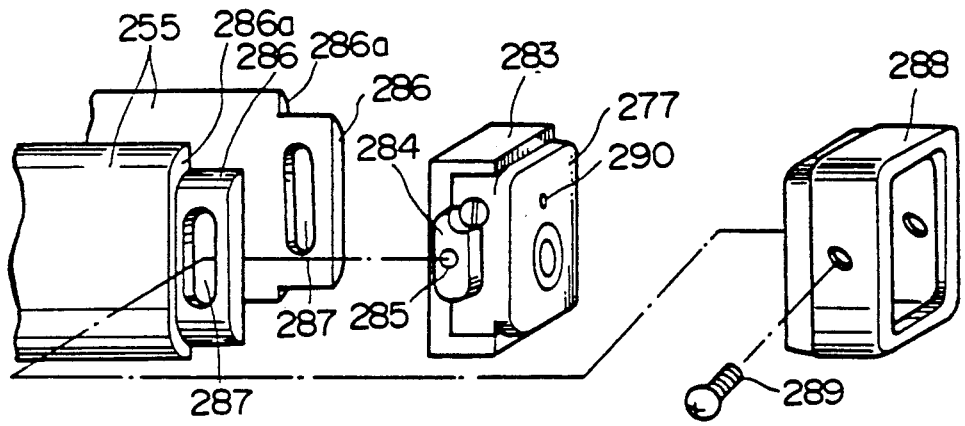

In FIG. 26, an insulating plate 283, formed of an electric insulating material to be channel-shaped, is provided on the end surface on the slider side of the optical sighting tube connecting member 277. The lateral width of the optical sighting tube connecting member 277 is formed to be the same as the distance between the reinforcing plates 255 and elliptic projections 284 are provided on both side surfaces. Connecting parts 286, formed to be smaller in diameter by steps 286a, are provided in the rear end parts of the reinforcing parts 255. Elliptic fitting holes 287, in which the above mentioned projections 284 can be fitted, are provided in these connecting parts 286. The projections 284 are fitted into these fitting holes 287 by pushing and expanding the fitting holes 287 outward by utilizing the resiliency of the reinforcing parts 255.

The optical sighting tube connecting member 277 is fitted to the reinforcing parts 255 a ring 288 formed of an electric insulating material is then fitted to the connecting parts 286 of the reinforcing parts 255 and screws 289 are screwed into the screw holes 285 of the projections 284 to fix the assembly. As the reinforcing parts 255 are thereby prevented from expanding outward, the optical sighting tube connecting member 277 will be fixed to the reinforcing parts 255.

Figure 27:
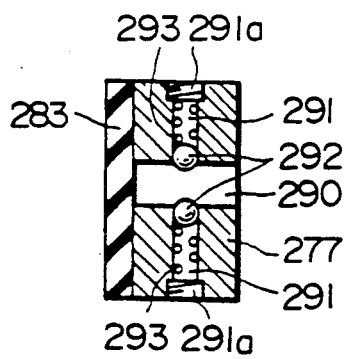
Figure 28:
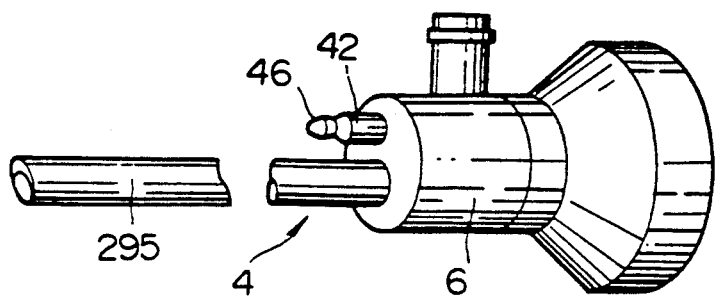
Figure 29:
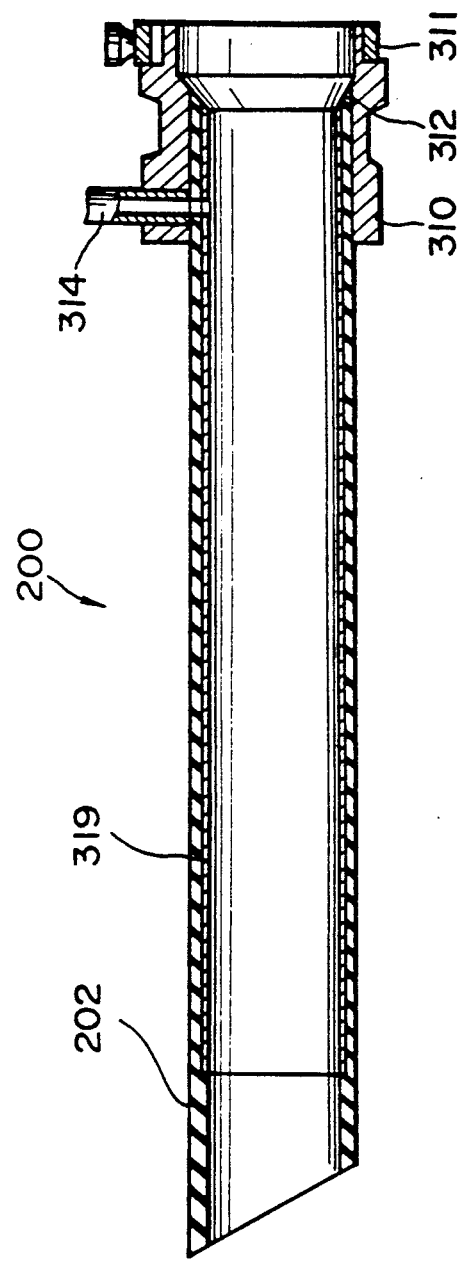
Figure 30:
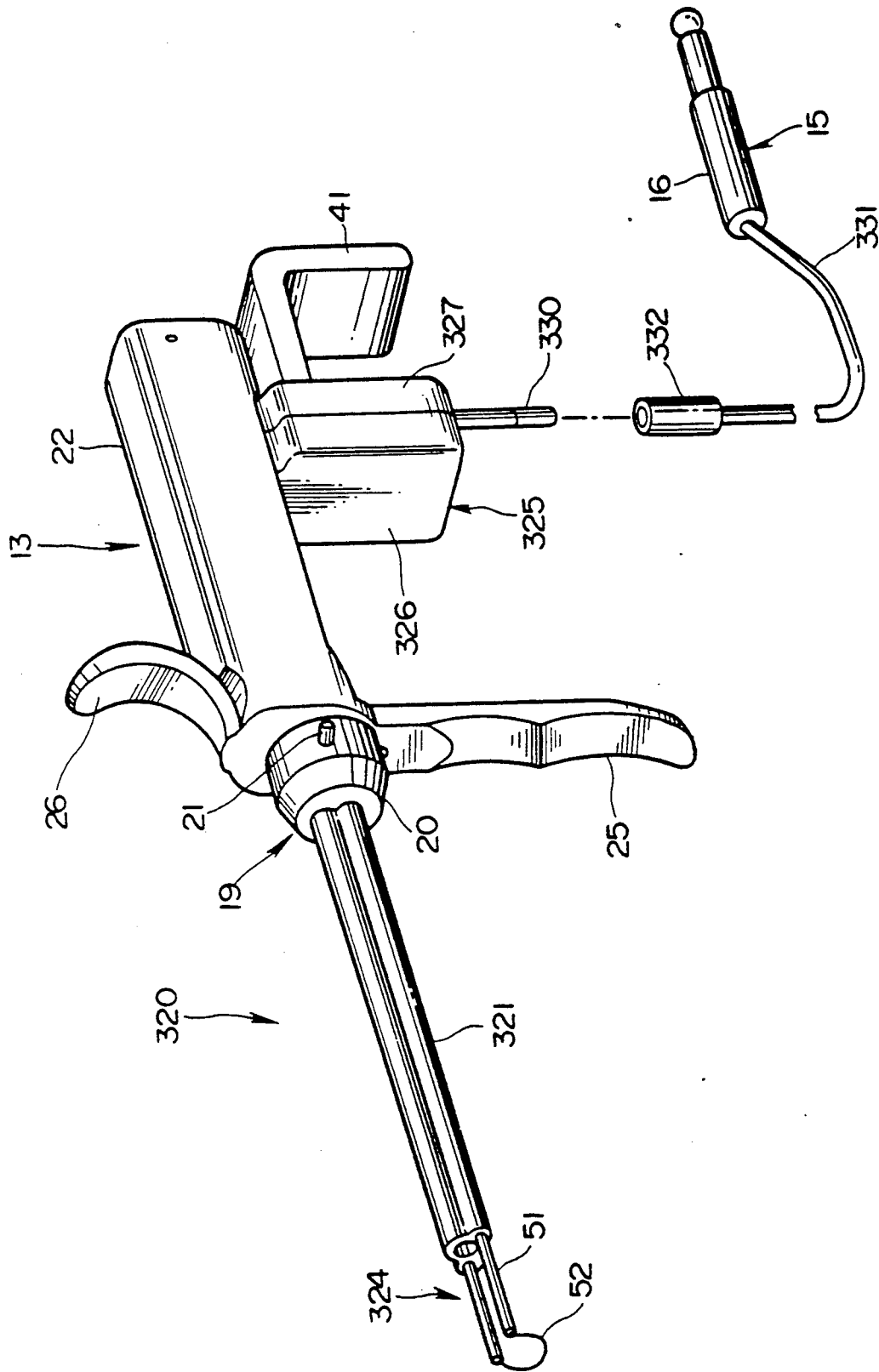
Figure 31:
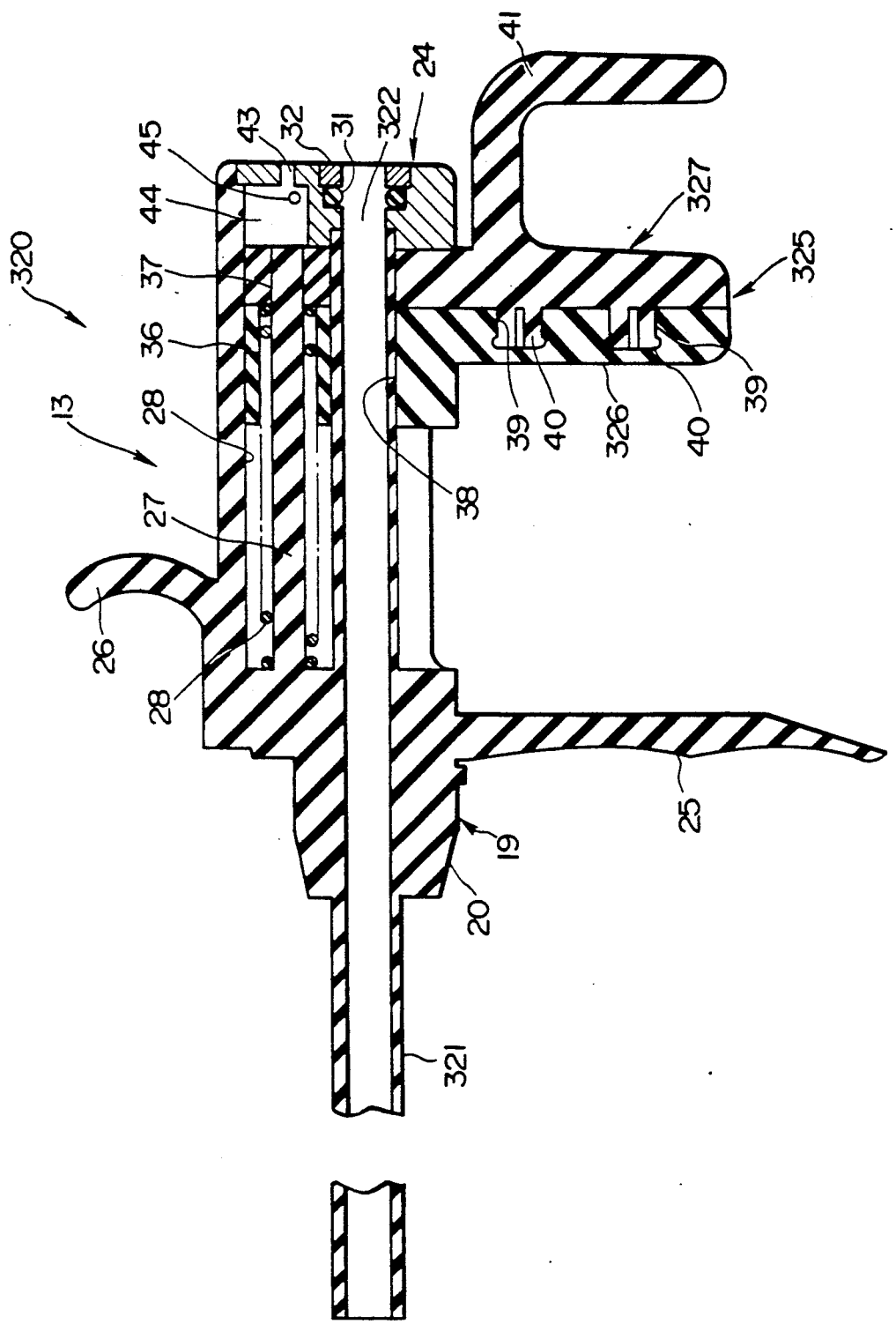
Figure 34:
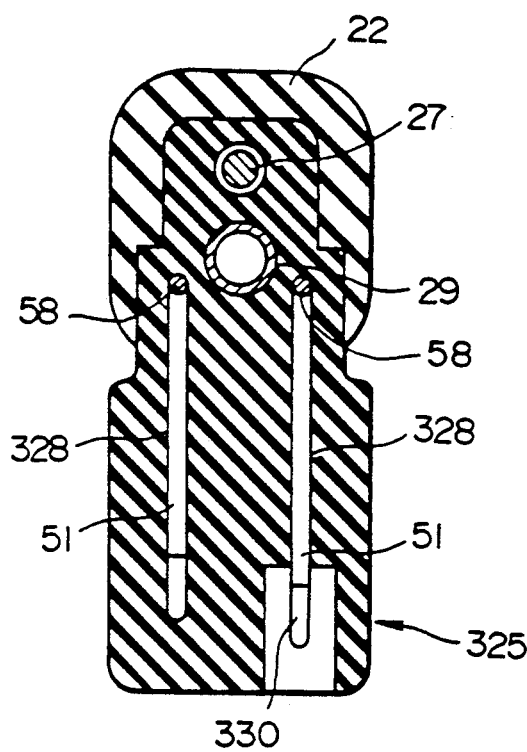

In FIGS. 27 and 28, the optical sighting tube 4 connecting mechanism shall be explained.

A connecting pin inserting hole 290 is provided as directed forward on the rear end surface of the above mentioned optical sighting tube connecting member 277 and a hole 291 passes at right angles with the connecting pin inserting hole 290. The inside diameter of the hole 291 in the position in which the hole 291 and inserting hole 290 communicate with each other is made smaller than the inside diameter of the outside of the hole 291 so that metal balls 292 may stand by as partly projected into the connecting pin hole 290 in this position. Each metal ball 292 is inserted into the hole 291 and is fixed by a coil spring 293 energized by a screw 291a screwed into the hole 291.

A connecting pin 42 is provided to project forward on the front end surface of the hand base part 6 of the optical sighting tube 4 and will be inserted into the above mentioned connecting pin inserting hole 290 when the inserted part 295 of the optical sighting tube 4 is inserted into the above mentioned optical sighting tube inserting hole 278. A groove 46 is provided around the tip part of the connecting pin 42. The metal balls 292 energized by the above mentioned coil springs 293 are engaged with this groove 46 to connect and fix the operating part 251 and optical sighting tube with each other.

Figure 22:
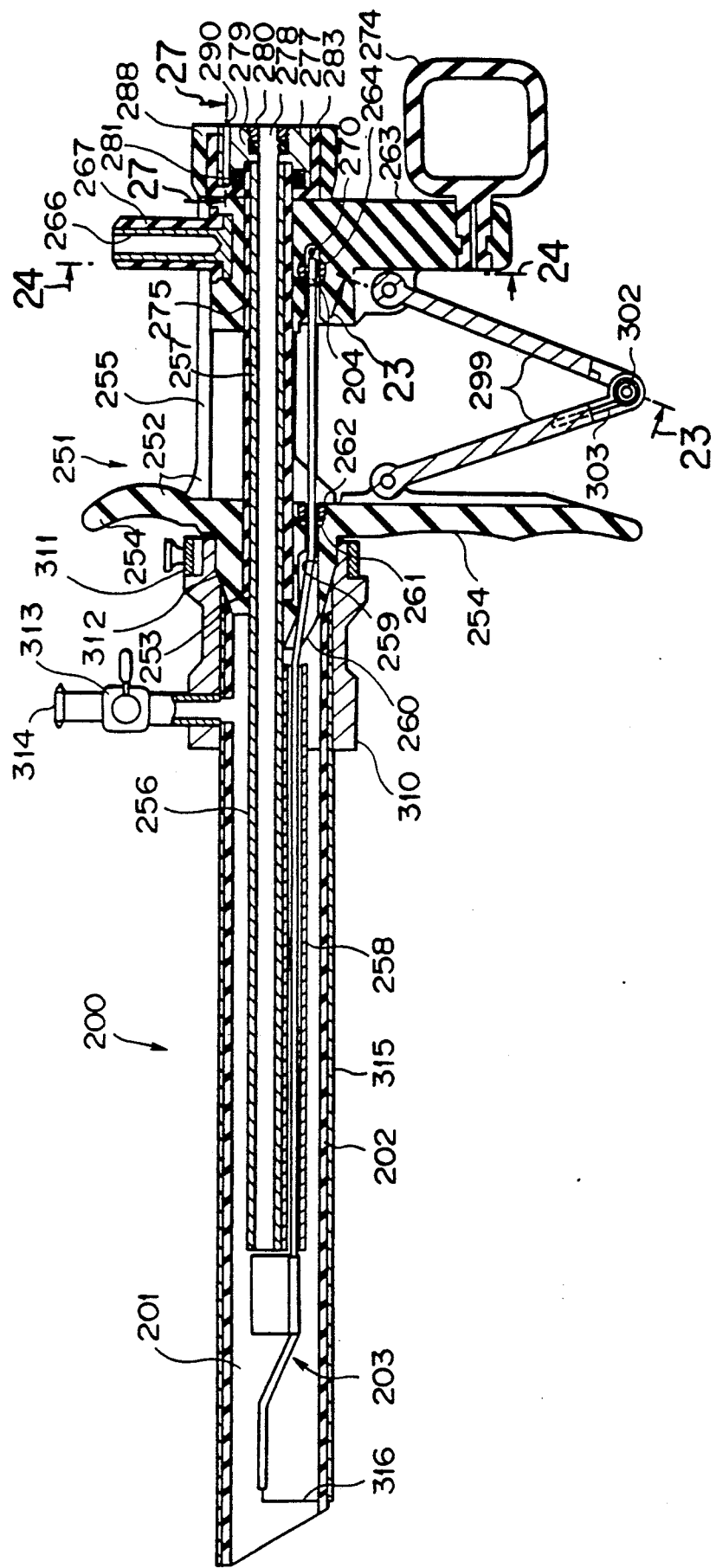

In FIG. 22, the finger hanger 254 and slider 263 are provided with link plates 299. The connecting part of the finger hanger 254 with the link plate 299 and the connecting part of the slider 263 with the link plate 299 are rotatably fitted by pressing a slit pin 301 into a set pin 300. The set pin 300 and slit pin 301 may be made of a metal or an electric insulating material such as plastic.

The above mentioned link plates 299 are rotatably connected with each other through a pin 302 provided with a coil spring 303. The slider 263 is energized to stand by in the rear of the operating part 251 by the operation of the link plates 299 and coil spring 303. When the thumb is put into the finger hanging ring 274 and the other fingers are placed on the finger hanger 254, if the thumb is pushed forward, the slider 263 will move forward and, if the force of the thumb is released, the slider 263 will be returned rearward by the energizing force of the coil spring 303.

The body 310 of the sheath 200 is removably connected with the sheath connecting part 253 of the operating part 251 through a cam ring 311 provided on the outer periphery on the 10 hand base side of the body 310 and a tapered part 312 provided on the inner periphery on the hand base side of the body 310. A water feeding port 314 fitted with a water feeding cock 313 is provided to project on the outer periphery on the tip side of the body 310.

A hollow tube part 201 is provided at the tip of the body 310 so as to lead the optical sighting tube 4 and electrode into a body cavity and is formed of a hollow inner tube 202 formed of an electric insulating material such as plastic and an outer tube 315 made of a metal and covering the inner tube 202 over the entire length to protect it. In order to reinforce the inner tube 202 made of plastic, instead of the outer tube 315, a reinforcing tube 319 made of a metal may be provided inside the inner tube 202 as in FIG. 29.

The electrode 203 is inserted into the electrode inserting tube 258 of the operating part 251 from the front end part, is passed through the electrode inserting hole 259 and O-ring 261 of the sheath connecting part 253 through the guide 60, is inserted into the electrode inserting hole 269 provided in the slider 263 and electrode receptacle 264 until it butts at the rear end against the positioning pin 270 and is fixed to the electrode receptacle 264 by the tip part of the set screw 271. In the front end part of the electrode 203, a loop 316 is formed arcuately with an inside diameter slightly smaller than the inside diameter of the inner tube 202 of the sheath 200 and is electrically connected with the electrode receptacle 264. The electrode 203 is insulated and coated except on the loop 316 and the rear end part 204 to be inserted into the electrode receptacle 264.

As in the above, the electrode 203 is enclosed with the inner tube 202 of the sheath 200 formed of an insulating material and the sheath connecting part 253 of the operating part 251 formed of the same insulating material, is further covered on both sides with the reinforcing parts 255 made of an insulating material and projecting from both sides of the sheath connecting part 253, is completely contained in its rear end part 204 in the slider 263 also made of an insulating material and is therefore enclosed and protected from outside with the insulating material over the entire length.

The operation is the same as in the first embodiment.

In this embodiment, in case the electrode 203 is broken, it will be able to be easily replaced by rotating the grip 272 of the slider 263.

As the slider 263 is slidably held from the right and left by the reinforcing parts 255, even in case the slider 263 is slid in the forward and rearward direction, the slider 263 will not rotate and the entire apparatus will be able to be made high in strength.

The other effects are the same as in the first embodiment.

FIGS. 30 to 35 show the fourth embodiment of the present invention.

In this embodiment, a guide tube is provided with an electrode inserting hole and is formed integrally with the body.

Figure 35:
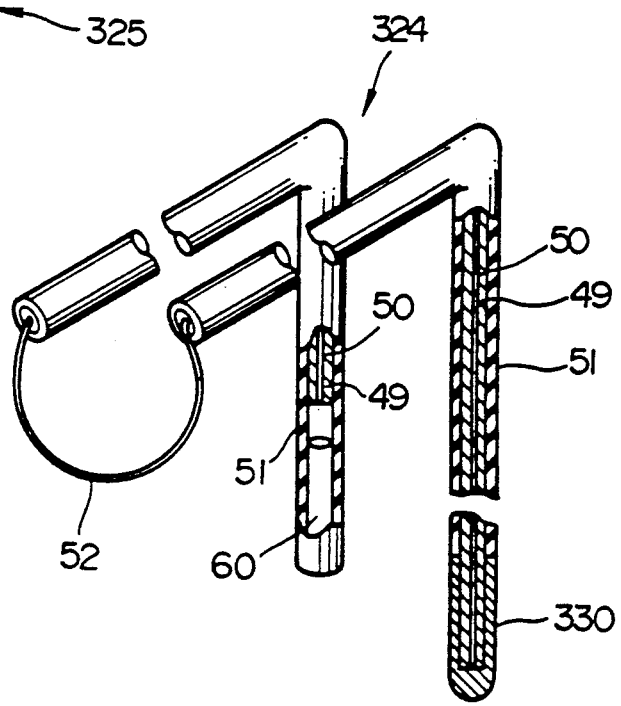

In this embodiment, an operating part 320 is molded integrally with a guide tube 321 of an electric insulating material such as plastic. This guide tube 321 is provided in the lengthwise direction with an optical sighting tube inserting hole 322 which is provided parallelly on both sides of the lower part with electrode inserting holes 323 as in FIG. 33. Electrode parts 324 are inserted through these electrode inserting holes 323 so as to come to a slider part 325 through a sheath connecting part 19. The electrode 324 is bent downward within the spaces 58 provided between the slider front part 326 and slider rear part 327 formed of an electric insulating material such as plastic. The end part of one of the electrode parts 324 leads to a groove 59 provided between the slider front part 326 and slider rear part 327 from the space 58. The end part of the other of the electrode parts 324 is exposed out of the slider part 325 through a groove 328 provided between the slider front part 326 and slider rear part 327 from the space 58. As shown in FIG. 35, the end part of this exposed electrode part 324 is connected with a plug 330 made of a metal as connected to a wire 50 and can be removably connected with the connector 332 provided at the other end of the cord part 331.

The other formations are the same as the operating part 3 of the first embodiment.

In this embodiment, the hollow tube part 336 of the sheath 335 is formed of a hollow pipe 337 made of a metal and a beak 338 provided at the tip of the hollow pipe 337, formed of a heatproof electric insulating material such as plastic and covering the electrode part 324 from the loop 52 at the tip to near the tip of the electrode inserting hole 323 of the operating part 320.

The other formations are the same as in the third embodiment.

Figure 36:
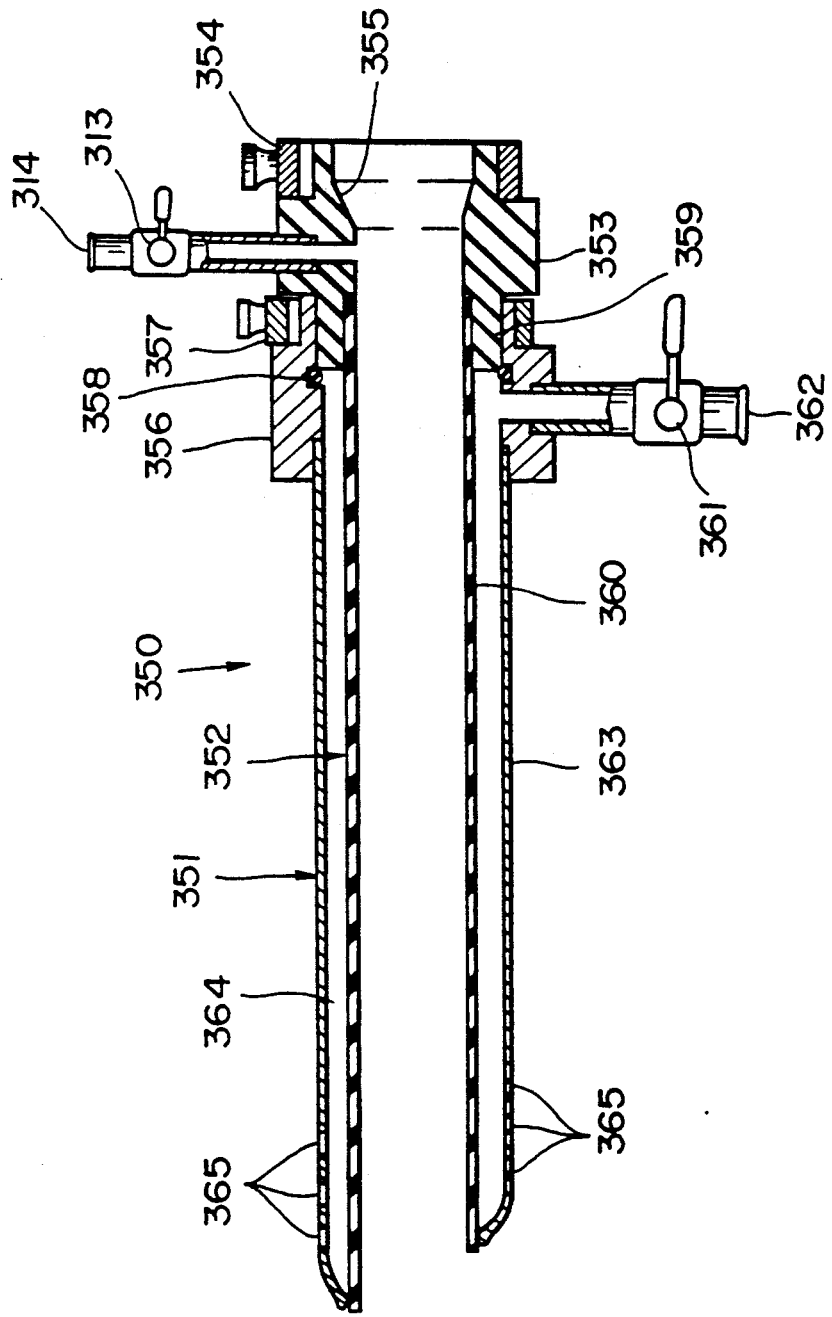
FIG. 36 relates to the fifth embodiment of the present invention and is a sectioned view of a sheath.

FIG. 36 shows the fifth embodiment of the present invention.

In this embodiment, the sheath 2 of the resectoscope apparatus 1 of the first embodiment is only different but the operating part 3, optical sighting tube 4 and mandolin 65 are the same as of the first embodiment.

In this embodiment, a (lasting irrigation type) sheath 350 is formed of an outer sheath 351 and inner sheath 352 so that water may be simultaneously fed and drained.

A cam ring 354 which can removably connect the sheath connecting part 19 of the operating part 3 is provided on the outer peripheral wall on the hand base side of the body 353 of the inner sheath 352 and a tapered part 355 is provided on the inner peripheral wall. A water feeding port 314 having a water feeding cock 313 is provided to project on the outer periphery near the middle of the body 353 and an outer sheath connecting part 359 is provided on the outer periphery on the tip side so as to be removably connectable to a ca ring 357. O-ring 358 is provided respectively on the outer wall and inner wall on the hand base side of the body 356 of the outer sheath 351. The body 353 is formed of an electric insulating material such as plastic. The hollow tube part 360 provided on the tip side of the body 353 is formed also of the electric insulating material such as plastic and forms a tube path through which the optical sighting tube 4 and electrode 5 can be inserted.

A water draining hole 362 having a water draining cock 361 is provided on the middle outer periphery of the body 356 of the outer sheath 351. An outer tube 363 is provided on the tip side so as to enclose the hollow tube part 360 of the inner sheath 352. The inside diameter at the tip of the outer tube 363 is substantially the same as the outside diameter of the hollow tube part 360 to clog the space 364 but the inside diameter on the hand base side from it is made large enough than the outside diameter of the hollow tube part 360 so that a space 364 large enough to flow drain water may be secured. A plurality of water draining holes 365 passing through the space 364 are provided on the outer periphery on the tip side of the outer tube 363.

As in the above, in this embodiment, water is fed from the water feeding port 314 and is led into a body cavity through the hollow tube part 360 and at the same time is drained out of the water draining port 362 through the space 364 from the water draining hole 365, irrigation can be always made and the visual field can be always kept clean.

The other effects are the same as in the first embodiment.

Figure 37:
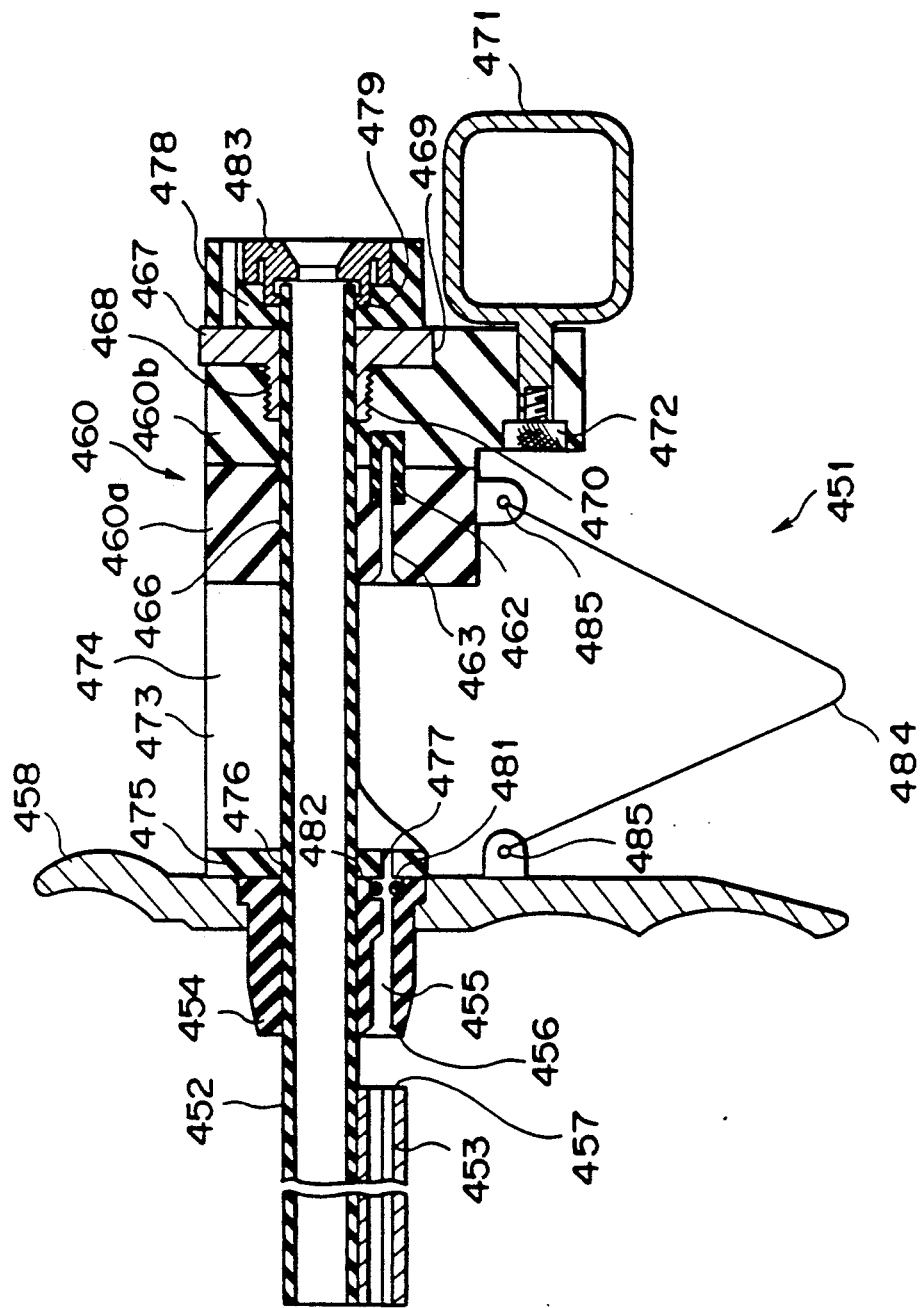
FIGS. 37 and 38 relate to the sixth embodiment of the present invention.
Figure 38:
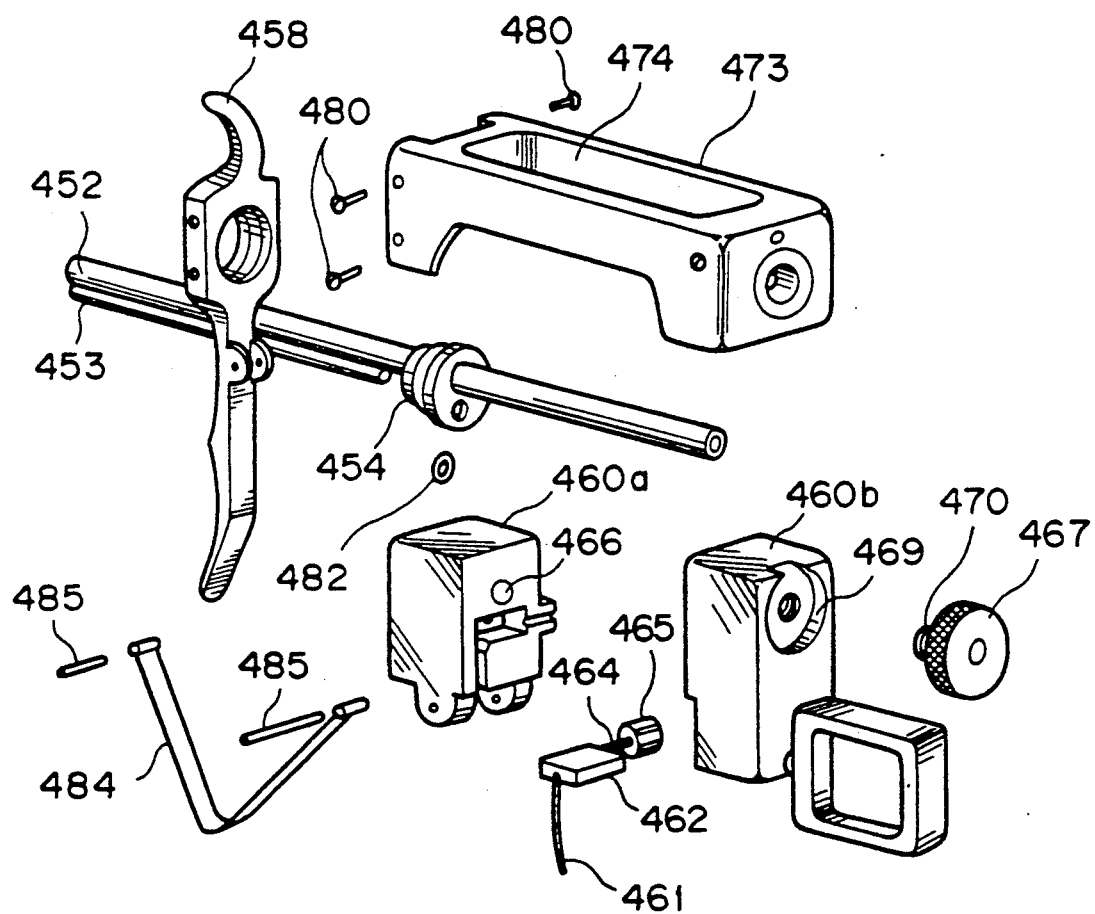

FIGS. 37 and 38 show the sixth embodiment of the present invention.

In this embodiment, against the third embodiment, the pair of reinforcing parts and fixing part of the operating part are made integral and the whole is formed to be box-like to improve the strength of the reinforcing parts.

On the tip side of a guide tube 452, formed of an insulating material of an operating part 451, an electrode inserting tube 453 is parallelly secured. On the hand base side at a small distance from the rear end of the electrode inserting tube 453, a sheath connecting part 454, formed of an insulating material such as plastic, is secured and is positioned so that the electrode inserting tube 453 and an electrode inserting hole 455 provided in the sheath connecting part 454 and greatly chamfered in the front part 456 may be aligned with each other.

A vertically projecting finger hanger 458 is bonded to this sheath connecting part 454 and sheath connecting pins 459 are fitted on the right and left. The finger hanger 458 and sheath connecting pin (not illustrated) may be formed of plastic or metal.

A slider 460 consists of a slider front part 460a and slider rear part 460b formed of an insulating material such as plastic, inserts within it an electrode receptacle 462 to which an electrode cord 461 is extended and is made integral by such means as bonding. The above mentioned slider front part 460a and electrode receptacle 462 are provided with an electrode inserting hole 463 into which a set screw 464 is screwed from outside the side of the slider 460 so as to be free to project and retreat at the tip. A grip 465 made of an insulating material is fitted to the rear end of this set screw 464.

The slider front part 460a and slider rear part 460b are provided with a guide tube inserting hole 466 of a diameter the same as or a little larger than the outside diameter of the guide tube 452. At the rear end of the slider rear part 460b, a screw 468 and a circular groove 469 incised in the upper part for fitting and housing a later described adjusting ring 467 are provided coaxially with the above mentioned guide tube inserting hole 466.

The above mentioned adjusting ring 467 is like a disc having in the center a hole through which the guide tube 452 is inserted, has an outside diameter in which a part of the outer periphery projects through an incision of a groove 469 and is so formed that, by rotating the projected outer periphery, the forward formed screw part 470 may be screwed into the screw 468 of the slider rear part 460b and the position of the slider 460 may be adjusted in the axial direction. On the lower part of the rear end surface of the above mentioned slider rear part 460b, a finger hanging ring 471 is rotatably fitted rearward by a screw 472.

A reinforcing part body 473 is like a frame inside which the slider 460 can be inserted and a large space 474 of a size movable forward and rearward is formed. The front part 475 of this body 473 is provided with a guide tube inserting hole 476 and electrode inserting hole 477. The guide tube 452 passes through this guide tube inserting hole 476, projects inside the body 473, passes through the guide tube inserting hole 466 of the slider 460 inserted into the space 474 of the body 473 and is fitted at the rear end into a hole 479 provided in the rear part 478 of the body 473. The guide tube 452 is not secured to the body 473 but is fixed by fitting the finger hanger 458 to the body with screws 480.

That is, by removing the screws 480, the finger hanger 458 together with the sheath connecting part 454 and guide tube 452 can be separated from the body 473 and therefore the slider 460 can be also simply removed.

An O-ring 482 securing the watertightness in case an electrode (not illustrated) is inserted is fitted to the rear part 481 of the electrode inserting hole 455 of the sheath connecting part 454. A rubber cap 483 securing the watertightness, when an optical sighting tube (not illustrated) is inserted, is fitted into a hole 479 of the rear part 478 of the body 473.

Between the finger hanger 458 and slider 460, a V-shaped plate spring 484 is rotatably fitted with pins 485 so that slider 460 may be energized by the plate spring 484 to be in contact with the rear part 478 of the body 473.

As in the above, in this embodiment, as the reinforcing part and fixing part are integrally formed to be like a box, a higher strength can be kept against twisting and tension.

Figure 39:
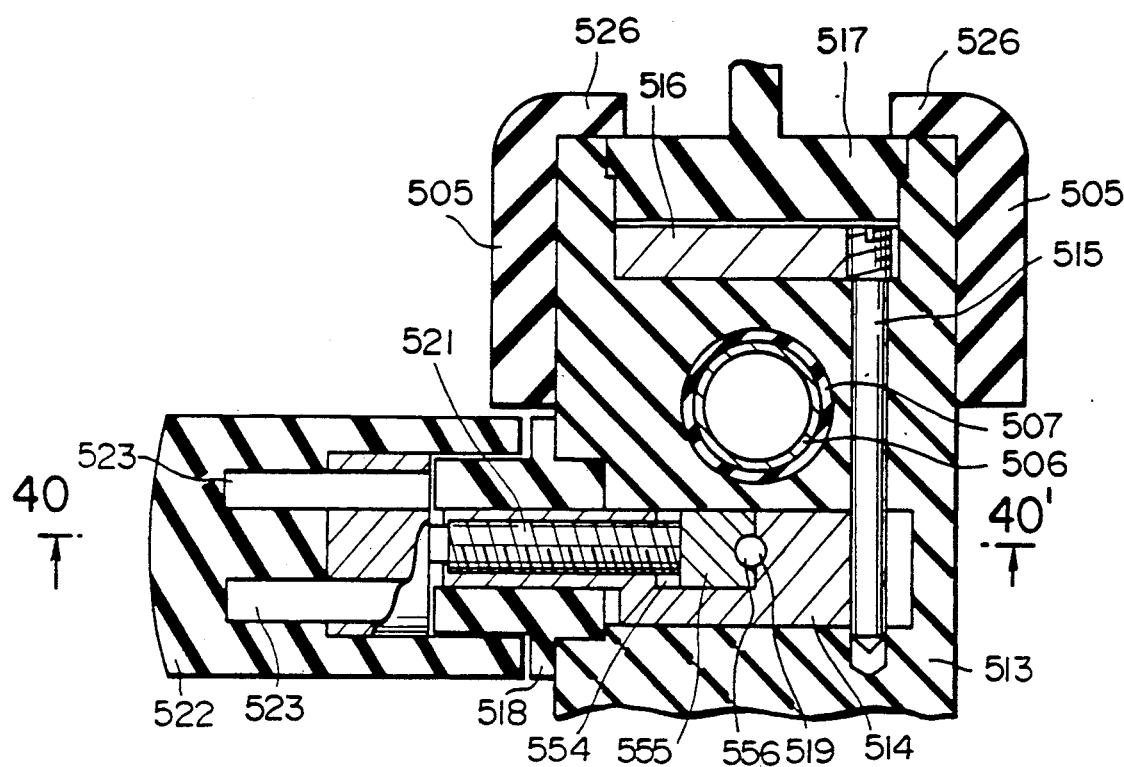
FIGS. 39 and 40 relate to the seventh embodiment of the present invention.
Figure 40:
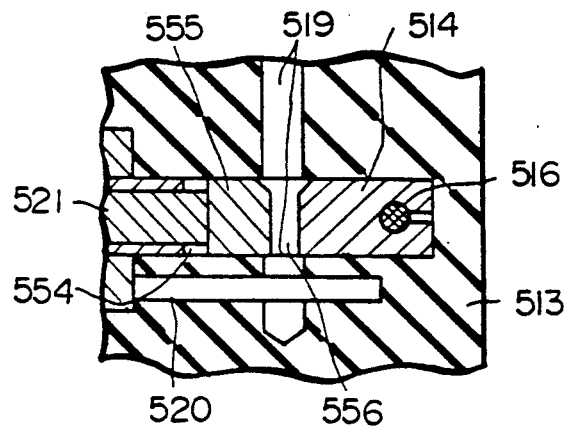
Figure 41:
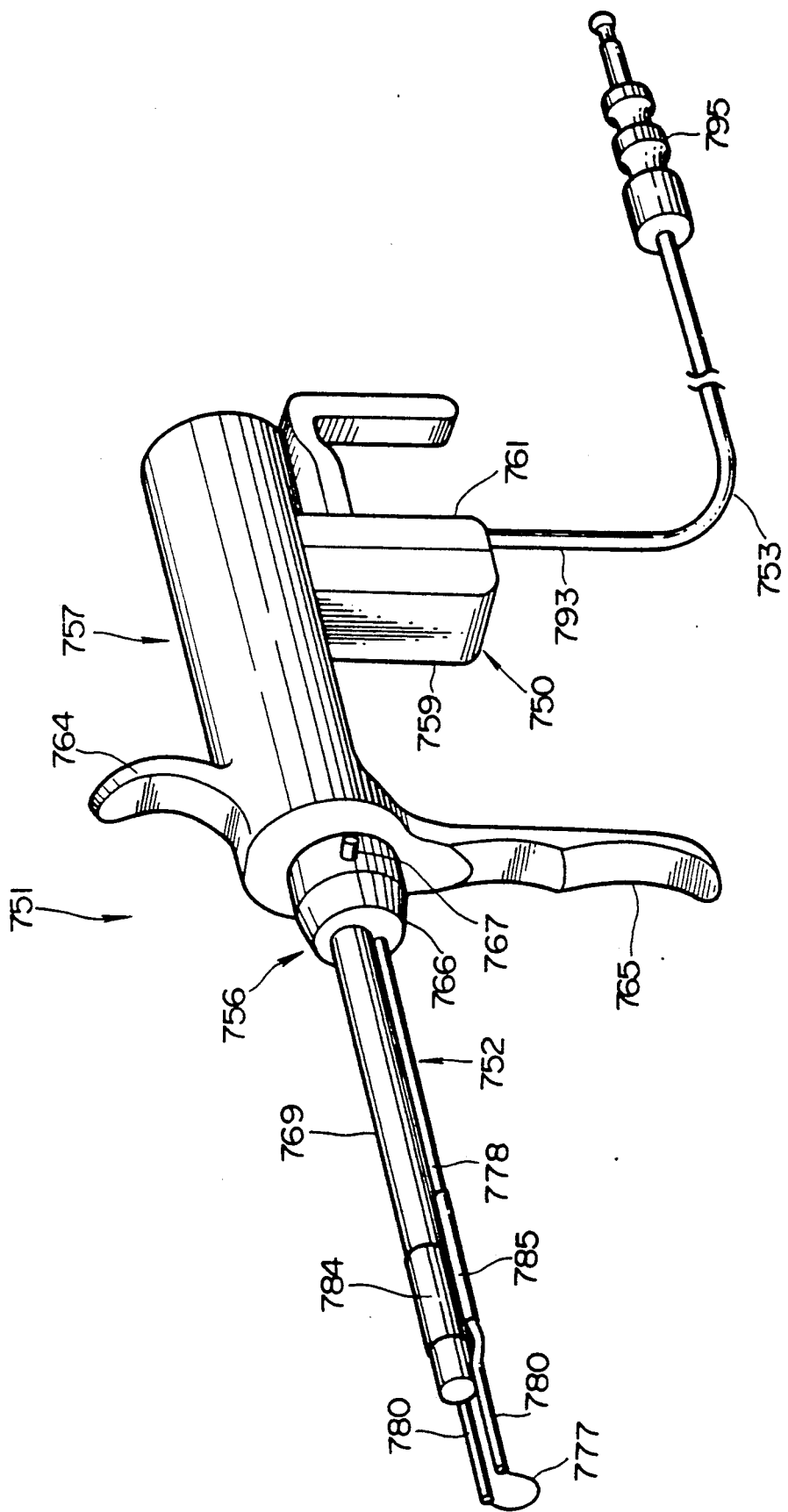
FIGS. 41 to 45 relate to the eighth embodiment of the present invention.
Figure 42:
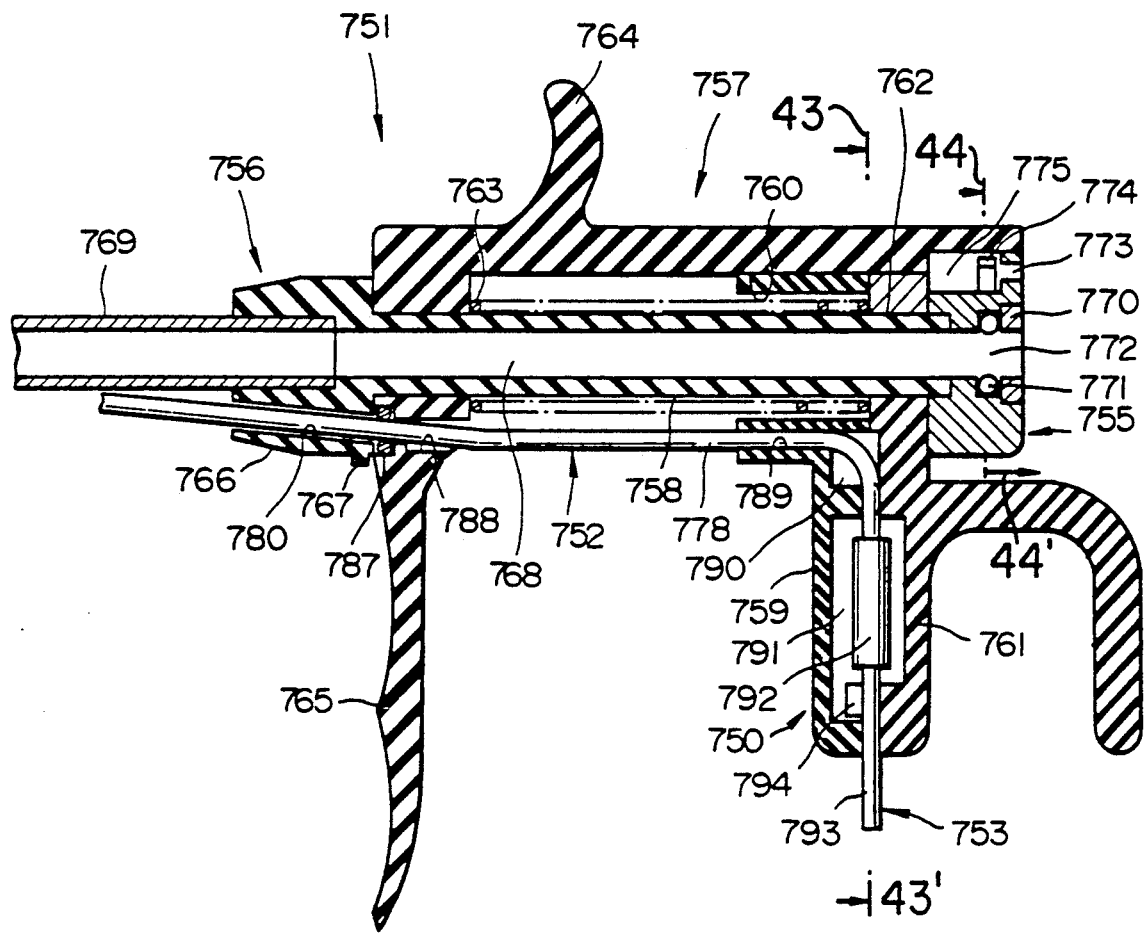
Figure 45:
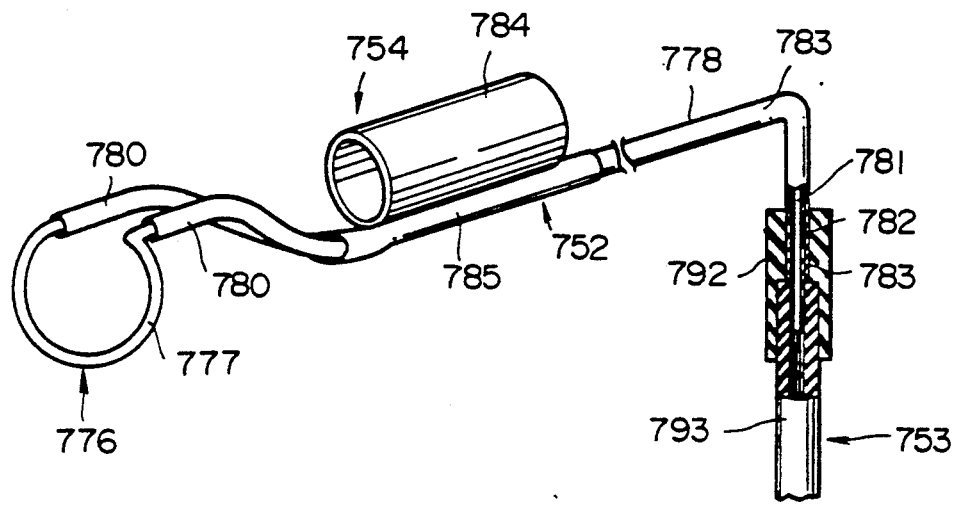
Figure 43:
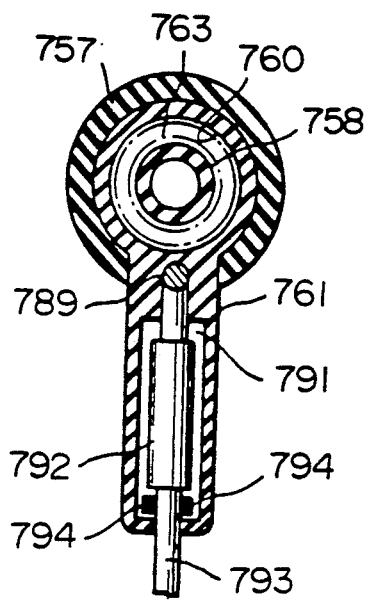
Figure 44:
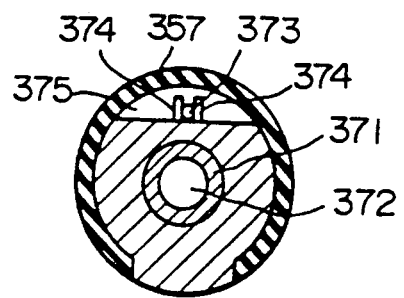

FIGS. 39 and 40 show the seventh embodiment of the present invention.

In this embodiment, the formation of the electrode receptacle 264 of the slider 263 in the operating part 251 in the third embodiment is only modified but the others are the same as in the third embodiment.

In this embodiment, the electrode receptacle 514 is provided with an incision 554 into which an electrode presser 555 is slidably fitted by half incising the electrode inserting hole 519. This electrode presser 555 is provided in the position opposed to the half incised electrode inserting hole 519 of the electrode receptacle 514 with a recess 556 having substantially the same radius of curvature as the electrode inserting hole. The depth of this recess is smaller than the radius of the shaft part of the electrode (not illustrated). The set screw 521 rotatably contacts at the tip with the electrode presser 555.

The other formations are the same as in the third embodiment.

In this embodiment, when fitting the electrode (not illustrated) to the operating part 501, when the set screw 521 is first loosened and the electrode is inserted into the electrode inserting pipe 508 from the tip, the electrode will be led to the electrode inserting hole 519 of the slider 513 through the electrode inserting hole 509 of the sheath connecting part 503. The electrode having entered the electrode inserting hole 519 will be inserted until it butts the positioning pin 520 while pushing the electrode presser 555 outward. When the set screw 521 is then fastened, the electrode presser 555 will be pressed toward the electrode inserting hole 519 side by the set screw 521 and therefore the electrode will be able to be held and fixed with the electrode receptacle 514 and electrode presser 555.

In the third embodiment, as the electrode is pressed directly by the set screw 521, the electrode has been likely to be crushed and deformed, to catch in the electrode inserting hole 519 and to become hard to remove.

In this embodiment, as the electrode is pressed by the recess of the electrode presser 555, there is an advantage that the electrode will not be deformed as in the above.

The other operations and effects are the same as in the third embodiment.

The eighth embodiment of the present invention is shown in FIGS. 41 to 45.

An operating part 751 comprises an electrode 754 in which an electrode part 752 and cord part 753 are integrally formed, an optical sighting tube connecting part 755 inserting and connecting the optical sighting tube 4 (See FIG. 28), a slider part 750 sliding the electrode 754 forward and rearward, a sheath connecting part 756 and a body 757.

The body 757 is formed to be like a cylinder of plastic opened on the lower side and in the rear. Substantially in the center of the cylinder of this body 757, an insulating pipe 758 is provided from a sheath connecting part 756 connected to the front of the body 757. This insulating pipe 758 is extended as integrally molded of plastic to the optical sighting tube connecting part 755 connected to the rear opened end of the body 757 through a spring hole 760 of a slider front part 759 forming a slider part 750 slidably fitted to the inside wall of the cylinder and a guide hole 762 of a slide rear part 761. A spring 763 is wound around the insulating pipe 758, is inserted through a spring hole 760 of the slider front part 759 and butts against the front surface of the slider rear part 761 so as to energize the slider part 750 always rearward.

An upper finger hanger 764, on which the forefinger may be placed when the operating part 751 is held with one hand, is provided on the front upper side of the cylindrical body 757. A lower finger hanger 765, on which the middle finger and third finger may be placed, is provided on the lower side of the front end part. Both parts are molded of plastic integrally with the body 757.

On the side wall of the sheath connecting part 756, a tapered pin 766 and pin 767 are provided as integrally molded so as to be removably connectable with the sheath 2 (See FIG. 1). On the front surface, a guide tube 769, having the same inside diameter as of an optical sighting tube hole 768, is provided as communicating with the optical sighting tube hole 768 within the insulating pipe 758 so that the optical sighting tube 544 may be contained. The optical sighting tube hole 768 continues at the rear end to an optical sighting tube inserting hole 772 containing an O-ring 771 fixed to the optical sighting tube connecting part 755 by an O-ring presser 770 so that the optical sighting tube 4 inserted through the optical sighting tube inserting hole 772 may be led to the tip of the guide tube 769. Above the optical sighting tube inserting hole 772, a pin hole 773 in which the connecting pin 42 of the optical sighting tube 4 can be inserted is provided and, in front of the pin hole, a space 775 in which clicks 774, which can bite and hold the connecting pin 42, project with a width slightly smaller than the connecting pin hole diameter is provided as communicating with the pin hole 773 so that the optical sighting tube 4 may be removably connected.

A loop 777, formed so that the wire 776 may internally contact the inside wall of the sheath 2, is provided at the tip of the electrode part 752, is extended substantially parallelly with the guide tube 769 rearward from both ends on the upper side of the loop 777, is bent downward along the outer periphery of the above mentioned guide tube 769 near the tip of the guide tube 769, is combined into one below the guide tube 769 and is connected to a shaft 778. The loop 777 is coated with stainless steel pipes (not illustrated) from both ends on the upper side so as to increase the stiffness of the wire 776 and is further thereon insulated and coated with Teflon tubes 780. The wire 776 combined into one is pressed and fixed with a stainless steel pipe 782 coating wires 781 of the shaft 778, is further coated with a Teflon tube 783 and is coated on the Teflon tube 783 with a pipe 785 bonded with a stabilizer 784 so that the stabilizer 784 may be fitted slidably on the outer periphery of the guide tube 769 and the loop 777 may move forward and rearward in the axial direction of the guide tube 769. The shaft 778 is extended further rearward from the rear end of the pipe 785, is led to an electrode hole 789 of the slider front part 759 through an electrode hole 786 provided below the insulating pipe 768 of the sheath connecting part 756 and an O-ring 787 and communicating hole 788 provided on the front surface wall of the body 757 and communicating with the electrode hole 786, is bent downward at right angles within a space 790 connected with the electrode hole 789 and is electrically connected with a cord 793 of the cord part 753 through a thermocontracting tube 792 within a space 791 formed between the slider front part 759 and slider rear part 761. The cord 793 is bitten and held by a presser 794 provided within a space 791 of the slider rear part 761 and having a width slightly smaller than the outside diameter of the cord 793 so as not be pulled out of the slider rear part 761, is extended to the outside of the slider part 750 and is connected at the other end with a plug 795 connectable to a high frequency current source (not illustrated).

In this embodiment, as the reinforcing part is formed of a cylinder, the strength is further increased.

As described above, according to the present invention, the electrode is enclosed or covered over the entire length with an electric insulating material forming the operating part and sheath. The electrode, through which a high frequency current flows, can be perfectly electrically separated from the patient or operator. The electric current leaking through the conductive material of the operating part and sheath, in case the insulating coating material of the electrode is broken, can be prevented from flowing to burn or shock the patient or operator and the operation can be made safely.

The resectoscope apparatus of the present invention has effects that it has a strength high enough against the large twisting force applied to the holding part and the tension applied to the optical sighting tube fixing part by the forward and rearward motion of the slider and is high in durability. As a result, during the operation, there is no accident that the guide tube is removed from the sheath connecting part, the fixing part is removed from the guide tube, the bearing part is broken or an unintended tissue is resected. During the operation, the rotation of the slider by the large twisting force applied to the thumb hanger can be regulated, the smooth forward and rearward motion of the slider can be guaranteed and the prostate can be continuously resected. There is also no need to have a spare operating part always prepared.

What is claimed is:

1. A resectoscope apparatus comprising:
   an electrode for resecting or coagulating tissues within a body cavity by using a high frequency current;

a sheath having a hollow part which is made of an electric insulation, a part of said electrode inserted through said hollow tube part;

an operating part making said electrode operatable from outside the body cavity, said operating part made of electric insulation, a remaining part of said electrode inserted through said operating part wherein said hollow tube part and said operating part enclose said electrode within said electric insulation; and an endoscope inserted through said sheath and making the body cavity interior observable.

2. A resectoscope apparatus according to claim 1 wherein said sheath is formed of said hollow tube part internally inserting an insertable part of said endoscope and a sheath body part providing in a base end part of said hollow tube part and removably connected to a sheath connecting part provided in a front end part of said operating part, and said hollow tube part and sheath body part are made of electric insulation.

3. A resectoscope apparatus according to claim 1 wherein said sheath is formed of said hollow tube part internally inserting an insertable part of said endoscope, a sheath body part provided in a base end part of said hollow tube part and removably connected to a sheath connecting part provided in a front end part of said operating part and an inner tube provided within said hollow tube part and made of electric insulation.

4. A resectoscope apparatus according to claim 1 wherein said sheath is formed of said hollow tube part internally inserting an insertable part of said endoscope and made of electric insulation, a sheath body part providing in a base end part of said hollow tube part and removably connected to a sheath connecting part provided in a front end part of said operating part and a reinforcing tube internally fitted to an inner peripheral wall of said hollow tube part.

5. A resectoscope apparatus according to claim 1 wherein said sheath is formed of said hollow tube part internally inserting an insertable part of said endoscope, a sheath body part provided in a base end part of said hollow tube part and removably connected to a sheath connecting part provided in a front end part of said operating part and a tip member provided in a tip part of said hollow tube part and made of electric insulation, said sheath connecting part made of electric insulation.

6. A resectoscope apparatus according to claim 1 wherein said sheath is formed of said hollow tube part internally inserting an insertable part of said endoscope and made of electric insulation, a sheath body part provided in a base end part of said hollow tube part, removably connected to a sheath connecting part provided in a front end part of said operating part and made of electric insulation and an outer sheath internally inserting said hollow tube part and provided to form a path for flowing an irrigating liquid between said outer sheath and an outer peripheral wall of said hollow tube part.

7. A resectoscope apparatus comprising:

an electrode for resecting or coagulating tissues within a body cavity by using a high frequency current;

a sheath having a hollow part which is made of an electric insulation, a part of said electrode inserted through said hollow tube part;

an operating part making said electrode operatable from outside the body cavity, said operating part made of electric insulation, a remaining part of said electrode inserted through said operating part wherein said hollow tube part and said operating part enclose said electrode within said electric insulation; and an endoscope inserted through said sheath and making the body cavity interior observable, wherein said sheath is formed of said hollow tube part internally inserting an insertable part of said endoscope and sheath body part provided in a base end part of said hollow tube part and removably connected to a sheath connecting part provided in a front end part of said operating part and said hollow tube part and sheath body part are made of electric insulation, and wherein said operating part is formed of a) said sheath connecting part having a guide tube inserting the insertable part of said endoscope, b) a slider fixing said electrode and provided slidably in forward and rearward directions on said guide tube and c) a cover part having a groove part containing said slides, and inserting through said groove part said electrode leading to said slider through said sheath connecting part, said sheath connecting part and cover part are integrally molded, and said guide tube, sheath connecting part slider and cover part are made of electric insulation.

8. A resectoscope apparatus according to claim 1 wherein said operating part is formed by assembling a sheath connecting part connected with a sheath body part provided in a base end part of said sheath and a cover part containing slidably in forward and rearward directions a slider fixing said electrode.

9. A resectoscope apparatus according to claim 3 wherein said operating part is formed of a) said sheath connecting part connected directly with said inner tube and having a guide tube inserting the insertable part of said endoscope, b) a slider fixing said electrode and provided slidably in forward and rearward directions on said guide tube, c) a cover part having a groove part containing said slider, said cover part is a reinforcing part containing said electrode leading to said slider through said sheath connecting part and d) an insulating pipe externally fitted in a slider sliding position of said guide tube, said sheath connecting part and cover part are integrally molded, and said sheath connecting part, slider, cover and insulating piper are made of electric insulation.

10. A resectoscope apparatus according to claim 4 wherein said operating part is formed of a) said sheath connecting part connected directly with said hollow tube part and having a guide tube inserting the insertable part of said endoscope, b) a slider fixing said electrode and provided slidably in forward and rearward directions on said guide tube, c) a cover part inserting and containing said slider, said cover part is a reinforcing part containing said electrode leading to said slider through said sheath connecting part, and c) an insulating pipe externally fitted in a slider sliding position of said guide tube, said sheath connecting part slider and cover part are integrally molded, and said sheath connecting part, slider, insulating pipe and cover are made of electric insulation.

11. A resectoscope apparatus according to any one of claims 2, 3 and 4 wherein said operating part is formed of a guide tube inserting the insertable part of said endoscope, said sheath connecting part connected with said guide tube, a slider fixing said electrode and provided slidably in forward and rearward directions on said guide tube and a cover part having a groove part containing said slider and inserting in said groove part said electrode leading to said slider through said sheath connecting part, said guide tube, sheath connecting part and cover part are integrally molded and said guide tube, sheath connecting part, slider and cover part are made of electric insulation.

12. A resectoscope apparatus according to claim 5 wherein said operating part is formed of a guide tube internally inserted in said hollow tube part, said operating part is connected with said sheath so that a tip part of the operating part may be provided to be positioned in front of the tip part of said hollow tube part, said guide tube internally inserting the insertable part of said endoscope and said electrode, said sheath connecting part connected with said guide tube, a slider fixing said electrode and provided slidably in forward and rearward directions on said guide tube, and a cover part having a groove part containing said slider and inserting in said groove part said electrode leading to said slider through said sheath connecting part, said guide tube, sheath connecting part and cover part are integrally molded and said guide tube, sheath connecting part, slider and cover part are made of electric insulation.

13. A resectoscope apparatus according to claim 1 wherein said operating part is formed of sheath connecting part removably connected with said sheath and provided with a guide tube inserting an insertable part of said endoscope, a slider fixing said electrode and provided slidably in forward and rearward directions on said guide tube and a cover part inserting and containing said slider, said cover part is a reinforcing part extended to a rear of said sheath connecting part.

14. A resectoscope apparatus according to claim 13 wherein said cover part consists of a pair of reinforcing members and is fitted to said sheath connecting part provided integrally with a finger hanging part for moving said slider forward and rearward.

15. A resectoscope apparatus according to claim 13 wherein said cover part is formed in a shape of a box provided with said slider slidably within and said cover part is fitted to a rear of said sheath connecting part.

16. A resectoscope apparatus according to claim 13 wherein said operating part is formed by internally molding said sheath connecting part and a pair of reinforcing members, forming said cover part.

17. A resectoscope apparatus according to claim 13 wherein said operating part is formed by internally molding said sheath connecting part and said cover part, having a groove part in which said slider slides.

18. A resectoscope apparatus comprising:
an electrode resecting or coagulating tissues within a body cavity using a high frequency current;
a sheath having a hollow tube part made of electric insulation, a part of said electrode inserted through said hollow tube part;
an operating part making said electrode operatable from outside the body cavity, said operating part together with said hollow tube part enclosing said electrode when said electrode is retracted into said sheath and said operating part is made of electric insulation; and
an endoscope inserted through said sheath to be able to observe the body cavity interior.

* * * * *